United States Patent
Jeannin et al.

(10) Patent No.: US 12,171,866 B2
(45) Date of Patent: Dec. 24, 2024

(54) LIPID EMULSION FOR PARENTERAL NUTRITION COMPRISING GPC

(71) Applicants: BAXTER INTERNATIONAL INC., Deerfield, IL (US); BAXTER HEALTHCARE SA, Glattpark (CH)

(72) Inventors: Laurent Jeannin, Uccle (BE); Julien Hecq, Glattpark (CH)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 841 days.

(21) Appl. No.: 17/059,916

(22) PCT Filed: May 29, 2019

(86) PCT No.: PCT/US2019/034403
§ 371 (c)(1),
(2) Date: Nov. 30, 2020

(87) PCT Pub. No.: WO2019/232054
PCT Pub. Date: Dec. 5, 2019

(65) Prior Publication Data
US 2021/0322303 A1    Oct. 21, 2021

Related U.S. Application Data

(60) Provisional application No. 62/679,352, filed on Jun. 1, 2018.

(51) Int. Cl.
*A61K 9/10* (2006.01)
*A23D 7/005* (2006.01)
(Continued)

(52) U.S. Cl.
CPC .......... *A61K 9/0029* (2013.01); *A23D 7/0053* (2013.01); *A23D 7/011* (2013.01);
(Continued)

(58) Field of Classification Search
CPC ...... A61K 9/0029; A61K 9/107; A61K 31/14; A61K 31/202; A61K 31/232;
(Continued)

(56) References Cited

U.S. PATENT DOCUMENTS

| 4,626,527 A | 12/1986 | Wurtman et al. |
| 5,567,736 A | 10/1996 | Buchman et al. |

(Continued)

FOREIGN PATENT DOCUMENTS

| CN | 101277670 | 10/2008 |
| CN | 102348469 | 12/2014 |

(Continued)

OTHER PUBLICATIONS

Zeisel, SH (Choline: Human Requirements and Effects on Human Performance in: Food Components to Enhance Performance: Institute of Medicine (US) Committee on Military Nutrition Research; Marriott BM, editor. 1994; 20 pages) (Year: 1994).*

(Continued)

*Primary Examiner* — Ernst V Arnold
(74) *Attorney, Agent, or Firm* — K&L Gates LLP

(57) ABSTRACT

The present disclosure relates to parenteral nutritional formulations, including ready-to-use parenteral nutrition formulations. More particularly, the present disclosure is directed to lipid formulations or emulsions and multi-chamber containers comprising same, wherein the lipid emulsion contains glycerophosphorylcholine as a choline source. The present disclosure further relates to methods of providing choline to a patient in need of parenteral nutrition and methods of avoiding and/or treating choline deficiency and liver damage.

25 Claims, 7 Drawing Sheets

(51) Int. Cl.

| | |
|---|---|
| A23D 7/01 | (2006.01) |
| A23D 7/06 | (2006.01) |
| A23L 33/00 | (2016.01) |
| A23L 33/11 | (2016.01) |
| A23L 33/12 | (2016.01) |
| A23L 33/125 | (2016.01) |
| A23L 33/175 | (2016.01) |
| A61J 1/10 | (2006.01) |
| A61J 1/20 | (2006.01) |
| A61J 3/00 | (2006.01) |
| A61K 9/00 | (2006.01) |
| A61K 9/107 | (2006.01) |
| A61K 31/14 | (2006.01) |
| A61K 31/202 | (2006.01) |
| A61K 31/232 | (2006.01) |
| A61K 31/661 | (2006.01) |
| A61K 31/685 | (2006.01) |
| A61K 33/12 | (2006.01) |
| A61K 36/05 | (2006.01) |
| A61K 47/10 | (2017.01) |

(52) U.S. Cl.
CPC ............... *A23D 7/06* (2013.01); *A23L 33/11* (2016.08); *A23L 33/12* (2016.08); *A23L 33/125* (2016.08); *A23L 33/175* (2016.08); *A23L 33/40* (2016.08); *A61J 1/10* (2013.01); *A61J 1/2093* (2013.01); *A61J 3/002* (2013.01); *A61K 9/107* (2013.01); *A61K 31/14* (2013.01); *A61K 31/202* (2013.01); *A61K 31/232* (2013.01); *A61K 31/661* (2013.01); *A61K 31/685* (2013.01); *A61K 36/05* (2013.01); *A61K 47/10* (2013.01); *A23V 2002/00* (2013.01)

(58) Field of Classification Search
CPC .... A61K 31/661; A61K 31/685; A61K 36/05; A61K 47/10; A61K 9/0019; A23D 7/0053; A23D 7/011; A23D 7/06; A23L 33/11; A23L 33/12; A23L 33/125; A23L 33/175; A23L 33/40; A61J 1/10; A61J 1/2093; A61J 3/002; A61J 1/00; A23V 2002/00; A23V 2250/304; A61P 3/02
See application file for complete search history.

(56) References Cited

U.S. PATENT DOCUMENTS

| | | |
|---|---|---|
| 2005/0027004 A1 | 2/2005 | Kyle et al. |
| 2007/0029001 A1 | 2/2007 | Trouilly et al. |
| 2007/0085059 A1* | 4/2007 | Mora-Gutierrez ........ A61P 9/10 252/400.21 |
| 2007/0092579 A1 | 4/2007 | Trouilly et al. |
| 2010/0233280 A1 | 9/2010 | Driscoll |
| 2010/0261676 A1 | 10/2010 | Semenkovich et al. |
| 2011/0015160 A1 | 1/2011 | Kyle et al. |
| 2014/0274957 A1* | 9/2014 | Driscoll ................ A61K 45/06 514/276 |
| 2016/0000652 A1 | 1/2016 | Rose |
| 2016/0243061 A1 | 8/2016 | Widberg et al. |
| 2016/0260169 A1 | 9/2016 | Perez et al. |
| 2017/0189365 A1 | 7/2017 | Puder et al. |
| 2018/0000732 A1 | 1/2018 | Brito De La Fuente et al. |

FOREIGN PATENT DOCUMENTS

| | | |
|---|---|---|
| CN | 105682481 | 6/2016 |
| JP | 2009-502435 | 1/2009 |
| WO | WO9011753 * | 10/1990 ............... A61K 9/10 |
| WO | 2011/097273 | 8/2011 |
| WO | 2016/170388 | 10/2016 |

OTHER PUBLICATIONS

Singer et al. (Clinical Nutrition 2009;28:387-400) (Year: 2009).*
Le et al. (Prostaglandins, Leukotrienes and Essential Fatty Acids 2009; 81:165-170). (Year: 2009).*
Hartmann et al. (Journal of Surgical Research 2014; 189:32-40). (Year: 2014).*
China Office Action for App. No. 201980036172.5 dated Sep. 29, 2023 (10 pages).
Indonesia Office Action for App; No. P00202010603 dated Sep. 30, 2022 (3 pages).
India Office Action for Application No. 202017054720 mailed May 25, 2022 (6 pages).
European Office Action for App. No. 19 733 233.1-1105 dated Aug. 10, 2023 (8 pages).
European Office Action for App. No. 21 188 025.7-1105 dated Aug. 10, 2023 (9 pages).
China Office Action for App. No. 201980036172.5 dated Feb. 11, 2013 (4 pages).
Communication for EP Application No. 19 731 456.0-1105 mailed Oct. 10, 2021 (8 pages).
Japanese Office Action for App. No. P2020-564442 dated Jan. 10, 2023 (2 pages).
Japanese Office Action for App. No. P2020-564494 dated Jan. 10, 2023 (2 pages).
Japanese Office Action for App. No. P2020-564442 dated Jun. 2, 2003 (4 pages).
Nutrients, 2017, vol. 9, doi:10.3390/nu9040388.
Communication for EP Application No. 19 731 456.0 mailed May 6, 2022 (8 pages).
European Search Report for Application No. 22 19 3264 mailed Jan. 5, 2023 (13 pages).
Japanese Office Action for App. No. P2020-564494 dated Jun. 13, 2003 (4 pages).
International Search Report for PCT/2019/034403 mailed Sep. 19, 2019 (4 pages).
Maitreyi Raman et al.; Parenteral Nutrition and Lipids; vol. 9, No. 4, Apr. 14, 2017; p. 388 XP55620512, DOI: 10.3390/nu9040388.
Ketan Hippalgaonkar et al.; Injectable Lipid Emulsions-Advancements, Opportunities and Challenges; AAPS Pharmscitech, vol. 11, No. 4, Oct. 26, 2010, XP55202451; DOI: 10.1208/s12249-010-9526-5.
Calder et al.; Lipid emulsions in parenteral nutrition of intensive care patients: current thinking and future directions; Jan. 14, 2010; Intensive Care Medicine, Springer, Berlin, DE; XP019797373; ISSN: 1432-1238 1.
Van Aerde J. E. et al.; Intravenous Fish Oil Emulsion Attenuates Total Parenteral Nutrition-Induced Cholestatis in Newborn Piglets; Pediatric Research, Lippincott Williams & Wilkinds, New York, US; vol. 45, No. 2, Feb. 1, 1999; XP008069933; ISSN: 0031-3998.
European Office Action for App; No. 21 188 025.7-1105 dated Nov. 15, 2022 (8 pages).
Brazil Office Action for App. No. BR112020022737-4 dated May 29, 2023 (4 pages).
European Office Action for App; No. 19 733 233.1-1105 dated Nov. 16, 2022 (9 pages).
European Office Action for App; No. 19 731 456.0-1105 dated Nov. 16, 2022 (6 pages).
Hau et al. "The essentiality of arachidonic acid and docosahexaenoic acid", Prostaglandins, eukotrienes and Essential Fatty Acids 81 (2009), 165-170 (XP026557729).
China Office Action for Application No. 201980035783.8 mailed Dec. 27, 2022 (21 pages).
Communication for EP Application No. 19 733 233.1 mailed May 6, 2022 (5 pages).
Australian Office Action for App. No. 2019277344 dated Jan. 30, 2024 (4 pages).

(56) References Cited

OTHER PUBLICATIONS

China Office Action for App. No. 201980035783.9 dated Sep. 19, 2023 (16 pages).
Israeli Office Action for App. No. 279082 dated Nov. 14, 2023 (3 pages).
Israeli Office Action for App. No. 279083 dated Nov. 14, 2023 (4 pages).
Brazil Office Action for App. No. BR11020023226-2 dated Sep. 7, 2023 (4 pages).
Australian Office Action for App. No. 2019279867 dated Jan. 31, 2024 (4 pages).
Korean Office Action for App. No. 10-2020-7037549 dated May 8, 2024 (9 pages).

\* cited by examiner

LIPID EMULSION FOR PARENTERAL NUTRITION COMPRISING GPC

CROSS REFERENCE TO RELATED APPLICATIONS

This application is a 371 of International Application No. PCT/US2019/034403, filed on May 29, 2019, and claims the benefit of priority to U.S. Provisional Application No. 62/679,352, filed on Jun. 1, 2018, the entire contents which are incorporated herein by reference for all purposes.

TECHNICAL FIELD

The present disclosure relates to parenteral nutritional formulations, including ready-to-use parenteral nutrition formulations. More particularly, the present disclosure is directed to lipid formulations or emulsions and multi-chamber containers comprising same, wherein the lipid emulsion contains glycerophosphorylcholine as a choline source. The present disclosure further relates to methods of providing choline to a patient, in need of parenteral nutrition and methods of avoiding and/or treating choline deficiency and liver damage.

DESCRIPTION OF THE RELATED ART

It is known that choline deficiency is an issue especially with patients receiving parenteral nutrition because the endogenous production of choline from parenterally provided methionine is not sufficient (Buchman, Gastroenterology 137 (5), 2009, S119-S128). There is evidence that hepatic steatosis develops during parenteral nutrition as a result of such choline deficiency. In addition, memory and cognitive deficits and skeletal abnormalities have been described. Given that choline is crucial for the synthesis of acetylcholine, which is the most relevant neurotransmitter in cholinergic cells, a deficiency in choline may be connected to such memory deficits. Choline deficiency may also play a role in cellular apoptosis.

Therefore, choline is regarded as an essential nutrient and an adequate intake (AI) was defined for adult men as 550 mg/day (~8 mg/kg/day) and for women (425 mg/day). The upper tolerable limit (UL) for choline intake is 3.5 g/day in adults (~50 mg/kg/day). Normal plasma-free choline concentration in an average adult is from 10 to 15 nmol/mL. For infants aged between 0 and 6 months with a reference weight of 7 kg the adequate AI is about 18 mg/kg/day (0.17 mmol/kg/day or 125 mg/day of choline), which is significantly higher in comparison to adults. For infants aged between 7-12 months the adequate AI is assumed to be 17 mg/kg/day, corresponding to 150 mg/day of choline (Dietary Reference Intakes for Thiamin, Riboflavin, Niacin, Vitamin B6, Folate. Vitamin B12, Pantothenic Acid, Biotin, and Choline; Institute of Medicine (US) Standing Committee on the Scientific Evaluation of Dietary Reference Intakes and its Panel on Folate, Other B Vitamins, and Choline. Washington (DC): National Academies Press (US), 1998, Chapter 12).

Pediatric patients seem to be especially susceptible to choline deficiency. Choline is transported across the placenta against a concentration gradient by the mammary epithelial cells and newborns have some significantly higher plasma-free concentrations of choline compared to adults. This may reflect the importance of choline fix the development of children, potentially for brain development (Zeisel, The Journal of Pediatrics, 149 (5), Supplement, 2006, S131-S136). In addition, choline is secreted in breast milk. Parenteral formulations for pre-term and newborn children who require parenteral nutrition should therefore provide for an effective choline source, as choline may be required in significant amounts for phospholipid synthesis in the central nervous system, kidneys, liver, lung and skeletal muscle. Recommendations for choline supply to preterm infants currently spans a broad range of 8-55 mg/kg/day (Bernhard et at, Eur J Nutr (2018).

Choline is available as a dietary supplement as choline chloride or choline bitartrate and as lecithin. In food, choline exists in free and esterified forms as phosphocholine, glycerophosphocholine, phosphatidylcholine and sphingomyelin. Phosphocholine comprises about 40% of total choline in human breast milk, α-glycerophosphocholine makes up for about another 40% of total human milk choline. Orally ingested nutrients generally are readily absorbed via the intestines and directly provided to the liver. In plasma, choline is the major water-soluble compound, whereas phosphocholine and α-glycerophosphocholine concentrations are very low. Mean plasma concentration of α-glycerophosphocholine is only about 0.42 μmol/L (Bernhard et al 2018), so there was not much focus on this compound in the past.

At the same time, plasma-free choline concentration was found to be significantly below normal in PN patients despite the provision of the choline precursor methionine in the PN solution and even though the plasma methionine concentration is generally found to be high to normal in said patients (Compher et al, Journal of Parenteral and Enteral Nutrition 26 (1), 2002, 57). Phosphatidylcholine which is contained in lipid emulsions used for parenteral nutrition is also not converted to choline to any significant extent.

Free choline is not included in total parenteral nutrition as of today. Instead, as tree choline is the principal water-soluble component in plasma and chloride the major anion, choline chloride is currently deemed to be recommendable for parenteral nutrition in a dose of about 25 mg/kg/day for patients (Bernhard et al., 2018). Another choline source is, for example, CDP choline (sodium salt).

However, it was found during the investigations made by the inventors, that choline chloride may not be as optimal as currently believed in the community, in part due to difficulties in stably introducing choline chloride into lipid emulsions for parenteral nutrition. In addition, there is some evidence that the presence of choline chloride may lead to the degradation of vitamins, especially vitamins B1 and B12 (Coelho, 2002: Vitamin stability in premixes and feeds. A practical approach in ruminant diets. Proceedings of the 13th Annual Florid a Ruminant Nutrition Symposium, Gainesville FL, January 10-11, 127-145; Frye, 1994: The performance of vitamins in multicomponent premixes. Proc. Roche Technical Symposium, Jefferson, Georgia).

It was now found that the choline derivative glycerophosphocholine (GPC) of formula (I), (2-{[(2S)-2,3-dihydroxypropyl phosphonato]oxy}ethyl)trimethylazanium, which is also referred to as glycerophosphorylcholine, a-glycerophosphocholine, L-alpha-glycerylphosphorylcholine, choline alfoscerate or α-glycerophosphocholine, is a choline derivative which can advantageously be used in parenteral formulations as an efficient choline source for patients who receive parenteral nutrition. GPC is a water-soluble molecule and is contained in small amounts in various foods, such as red meat, but contents are generally rather low.

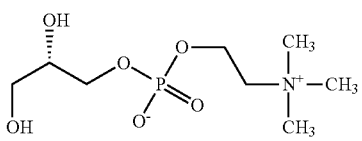
(I)

The majority of the GPC is made synthetically from natural phospholipids, such as are present in egg yolk or soybeans. For example, GPC is obtained from purified natural phosphatidylcholine (PC), which is hydrolyzed to remove the fatty acids. The GPC is then further reacylated and/or treated with specific enzymes to synthesize a specific chemical molecule (van Hoogevest and Wendel, Eur. J, Lipid Sci. Technol. 2014, 116, 1088-1107).

GPC has so far not been considered as a component and a choline source in lipid emulsions for use in parenteral nutrition.

U.S. Pat. No. 8,865,641 B2 discloses a method of treating a tatty liver disease in a subject comprising administering to the subject an effective amount of a cholinergic pathway stimulating agent, wherein the nicotinic receptor agonist may be choline. However, GPC and/or a lipid emulsion for parenteral nutrition are not mentioned.

U.S. Pat. No. 8,337,835 B2 describes a method of treating a peroxisome proliferator-activated receptor alpha (PPARα)-related liver disorder, lowering triglyceride levels, and/or elevating high density lipoprotein levels in a mammal, said method comprising administering a therapeutically effective amount of 1-palmitoyl-2-oleoyl-sn-glycerol-3-phosphocholine (16:0/18:1-GPC) to said mammal.

US 20110015154 A1 discloses compositions and kits containing a choline compound and a carnitine compound and methods for using the compositions and kits, wherein the choline compound may be alpha-GPC. However, US 20110015154 A1 does not describe lipid emulsions for parenteral nutrition comprising GPC and does not disclose relevant concentrations of GPC in such lipid emulsions for parenteral nutrition.

US 20150132280 A1 describes a dietary supplement for improving mood, energy, focus etc., comprising theacrine and optionally other compounds that modulate the effects of theacrine, including among an extensive list of optional additional compound s alpha-GPC. However, lipid emulsions for parenteral nutrition comprising GPC are not mentioned either.

SUMMARY

In light of the disclosure herein, and without limiting the scope of the invention in any way, in a first aspect of the present disclosure, which may be combined with any other aspect listed herein unless specified otherwise, a lipid formulation for parenteral administration to a patient in need of choline supplementation comprises glycerophosphocholine (GPC) in a concentration of from 0.1 g to 15.0 g per liter of the lipid emulsion. The lipid formulation has an aqueous phase and an oil phase, includes about 5% to about 35% by weight of the oil phase based on the total weight of the lipid formulation, and is present in the form of an oil-in-water emulsion.

According to one aspect, the lipid emulsion comprises GPC in a concentration of from 2.0 to 12.0 g per liter of lipid emulsion. According to another aspect, the lipid emulsion comprises GPC in a concentration of from 4.0 to 11.0 g per liter of lipid emulsion. Lipid emulsions having a higher concentration of GPC as described before are specifically useful for the treatment of pediatric patients.

According to another aspect, the lipid emulsion comprises GPC in a concentration of from 0.5 to 6.0 g per liter of lipid emulsion. According to another aspect, the lipid emulsion comprises GPC in a concentration of from 0.5 to 5.0 g per liter of lipid emulsion. According to yet another aspect, the lipid emulsion comprises GPC in a concentration of from 0.5 to 3.0 g per liter of lipid emulsion. Lipid emulsions having a lower concentration of GPC as described before are specifically useful for the treatment of adult patients.

According to another aspect of the invention, the lipid emulsion further contains docosahexaenoic acid (DHA) in a concentration of from 0.1 g to 15.0 g per 100 g of oil phase. According to one aspect, the lipid emulsion contains DHA in a concentration of from 0.25 g to 3.0 g per 100 g of oil phase. According to another aspect, the lipid emulsion contains DHA in a concentration of from 1.5 g to 2.5 g per 100 g of oil phase. According to yet another aspect DHA is present in triglyceride form or ethyl ester form, preferably in triglyceride form.

According to another aspect of the invention, the lipid emulsion further contains arachidonic acid (ARA) in a concentration of from 0.1 g to 15.0 g per 100 g of oil phase. According to one aspect ARA is present in a concentration of from 1.5 g to 7.5 g per 100 g of oil phase.

According to yet another aspect of the invention, the lipid emulsion is essentially free of eicosapentaenoic acid (EPA).

According to one aspect, the lipid emulsion comprises EPA, wherein the ratio between DHA and EPA is from 10:1 to 1000:1 (w/v), from 10:1 to 200:1 (w/v), from 10:1 to 100:1 (w/v) or from 1:1 to 10:1 (w/v).

According to one aspect of the invention, the lipid emulsion is provided in a single-chamber container for administration to a patient in need. Single-chamber containers can be flexible or rigid containers as well as glass vials.

According to one aspect of the invention, the lipid emulsion according to the invention is directly administered to the patient without admixing the lipid emulsion with other parenteral nutrition formulations, such as, for example, amino acid formulations or carbohydrate formulations.

According to yet another aspect, the lipid emulsion comprising from 0.5 g to 5.0 g GPC per liter is used for the treatment of adult patients in need of choline supplementation. Specifically, the lipid emulsion is used for patients suffering from liver steatosis.

According to another aspect, said lipid emulsion for direct administration comprises from 2.0 g to 12.0 g GPC per liter. According to yet another aspect, the lipid emulsion comprising from 0.2 g to 0.9 g GPC per liter is used for the treatment of adult patients in need of choline supplementation, Specifically, the lipid emulsion is used for patients suffering from liver steatosis.

According to another aspect, the said lipid emulsion for direct administration is provided to the patient after adding one or more compounds, such as, for example, trace elements and/or vitamins, to the emulsion before or at the time of administration, wherein the concentration of glycerophosphocholine in the administered lipid emulsion is not essentially changed.

According to another aspect of the invention, the lipid emulsion is provided as one of several components in a multi-chamber bag (MCB) which is designed for the parenteral administration of its reconstituted content after admixing the formulations contained in the respective chambers. Such MCB may have 2, 3, 4, 5, 6 or more chambers.

The chambers of said MCB may have the same size or may have different sizes to accommodate various compositions and volumes. The chambers may be designed to contain volumes of from, for example, 1 to 5 ml, from 5 to 10 ml, from 10 to 50 ml, from 50 to 100 ml, from 100 to 250 ml, from 250 ml to 500 ml, from 500 to 1000 ml, from 1000 to 1500 ml. The MCBs can be designed to have chambers which are located adjacent to each other. The chambers may have various shapes. The chambers can be oriented horizontally and/or vertically to each other. Certain small chambers can be designed to be located within another, larger chamber, wherein, for example, the small chamber which is located within another, larger chamber can be accommodated and fixed into said larger chamber by welding at least one edge of said small chamber in between the weld seam of the surrounding larger chamber.

According to one aspect, the multi-chamber container for parenteral administration of its reconstituted content includes the lipid emulsion according to the invention in a first chamber and a carbohydrate formulation or an amino acid formulation in a second chamber.

According to another aspect, the multi-chamber container for parenteral administration of its reconstituted content includes the lipid emulsion according to the invention in a first chamber, an amino acid formulation in a second chamber and a carbohydrate formulation in a third chamber. Optionally additionally the multi-chamber container includes a fourth chamber which comprises vitamins and/or trace elements.

According to yet another aspect, the multi-chamber container in addition to said first, second and third chamber includes a vitamin formulation in a fourth chamber and a trace element formulation in a fifth chamber.

According to another aspect, the multi-chamber container includes frangible barriers between the chambers which can be opened before use in order to mix the components of all or selected chambers.

According to another aspect, the lipid emulsion provided in a multi-chamber bag comprises GPC in a concentration of from 0.1 g to 15.0 g per liter.

According to yet another aspect, the lipid emulsion provided in a multi-chamber bag comprises GPC in a concentration of from 2.0 g to 12.0 g per liter.

According to yet another aspect, the lipid emulsion provided in a multi-chamber bag comprises GPC in a concentration of from 4.0 g to 11.0 g per liter. Such multi-chamber bag is preferably used in the treatment of pediatric patients who require parenteral nutrition.

According to yet another aspect of the present invention, the lipid emulsion provided in a multi-chamber bag comprises GPC in a concentration of from 0.5 g to 6.0 g per liter. According to yet another aspect of the present invention, the lipid emulsion provided in a multi-chamber bag comprises GPC in a concentration of from 0.5 g to 5.0 g per liter.

According to yet another aspect of the present invention, the lipid emulsion provided in a multi-chamber bag comprises GPC in a concentration of from 0.5 g to 3.0 g per liter. Such multi-chamber bag is preferably used in the treatment of adult patients who require parenteral nutrition.

According to yet another aspect of the present invention, the glycerophosphocholine is provided in a solution which is reconstituted from a multi-chamber bag and wherein the GPC is present in a concentration of from 0.01 g to 6.0 g per liter of reconstituted solution. According to one aspect, the reconstituted solution comprises glycerophosphocholine in a concentration of from 0.01 g to 2.0 g per liter. According to yet another aspect, the reconstituted solution comprises glycerophosphocholine in a concentration of from 0.5 g to 5.0 g per liter.

According to another aspect of the present invention, the glycerophosphocholine is provided in a parenteral nutrition composition which reconstituted from a multi-chamber container which comprising at least two, at least three, at least four, or at least five chambers, wherein at least one of the chambers is filled with an amino acid formulation, a carbohydrate formulation, or a lipid formulation, and wherein glycerophosphocholine is present in the composition in a concentration of from 0.01 g to 6.0 g per liter. According to one embodiment, the glycerophosphorylcholine is provided in a dual chamber bag or a three-chamber bag comprising at least one amino acid formulation and/or at least one carbohydrate formulation and/or at least one lipid formulation.

According to another aspect of the present invention, a method for providing choline to a patient is provided, wherein the patient requires parenteral nutrition and is in need of receiving choline, said method comprising administering a composition for parenteral administration which is characterized in that it comprises glycerophosphocholine in a concentration of from 0.01 g to 15.0 g per liter of the composition.

According to yet another aspect of the present invention, a parenteral nutrition solution for the treatment of choline deficiency in pediatric and/or adult patients is provided, wherein the solution comprises glycerophosphocholine in a concentration of from 0.01 g to 15.0 g per liter of the solution. According to one aspect, the parenteral nutrition solution is a lipid emulsion. According to another aspect, said lipid emulsion is a ready-to-use solution for direct administration to the patient. According to yet another aspect said lipid emulsion is one of at least two, three, four or five compositions provided separate chambers of a multi-chamber bag.

According to another aspect of the invention, the patient receiving glycerophosphocholine requires parenteral nutrition because oral and enteral nutrition is not possible, insufficient or contraindicated. According to one aspect, the patient suffers from choline deficiency or is at risk of developing choline deficiency. According to a further aspect, the patients suffers from hepatic steatosis or is at risk of developing hepatic steatosis. According to yet another aspect, the patient suffers from parenteral nutrition-associated liver disease, specifically hepatic steatosis.

According to yet another aspect of the present invention, the said method for providing choline to a patient comprises administering glycerophosphocholine in a dose of from 15 mg/kg/day to 300 mg/kg/day. According to one aspect, glycerophosphocholine is administered to a pediatric patient in a dose of from 24 mg/kg/day to 210 mg/kg/day, from 50 mg/kg/day to 150 mg/kg/day, and from 70 mg/kg/day to 100 mg/kg/day.

According to yet another aspect of the invention, the said method for providing choline to a patient comprises administering glycerophosphorylcholine to an adult patient in a dose of from about 5 mg/kg/day to 50 mg/kg/day, from 10 mg/kg/day to 30 mg/kg/day, and from 20 mg/kg/day to 30 mg/kg/day.

According to another aspect of the invention, the lipid emulsion or reconstituted solution comprising glycerophosphocholine is administered by means of a peripheral or central catheter.

BRIEF DESCRIPTION OF THE DRAWINGS

Understanding that figures depict only embodiments of the invention and are not to be considered to be limiting the scope of the present disclosure, the present disclosure is described and explained with additional specificity and detail through the use of the accompanying figure.

FIG. 3A shows that the administration of a lipid emulsion comprising GPC has the most significant impact on the development of vacuolation in comparison with all choline derivatives tested. FIG. 3B provides for the results of ad ministering again saline solution alone, a lipid emulsions (LE 13%) which has been supplemented with DHA and ARA (triangles) and a lipid emulsion (LE 13%) which has been supplemented with DHA, ARA and GPC (squares). FIG. 3B shows that the presence of DHA and ARA already has a significant positive effect on liver vacuolation. The expression "low" refers to a concentration of the respective choline derivative of 15 mmol/L. The expression "high" refers to a choline derivative concentration of 31 mmol/L. Grades are defined as provided for in Example 3.3.

FIG. 5 shows exemplary photographs of Grade 1 to 5 vacuolation determined in the histopathological analysis of the liver of study animals (see Examples 1 and 3). The histological slides shown were stained with hematoxylin-eosin. Grades were assigned according to the following scheme.

DETAILED DESCRIPTION

Figure 1:
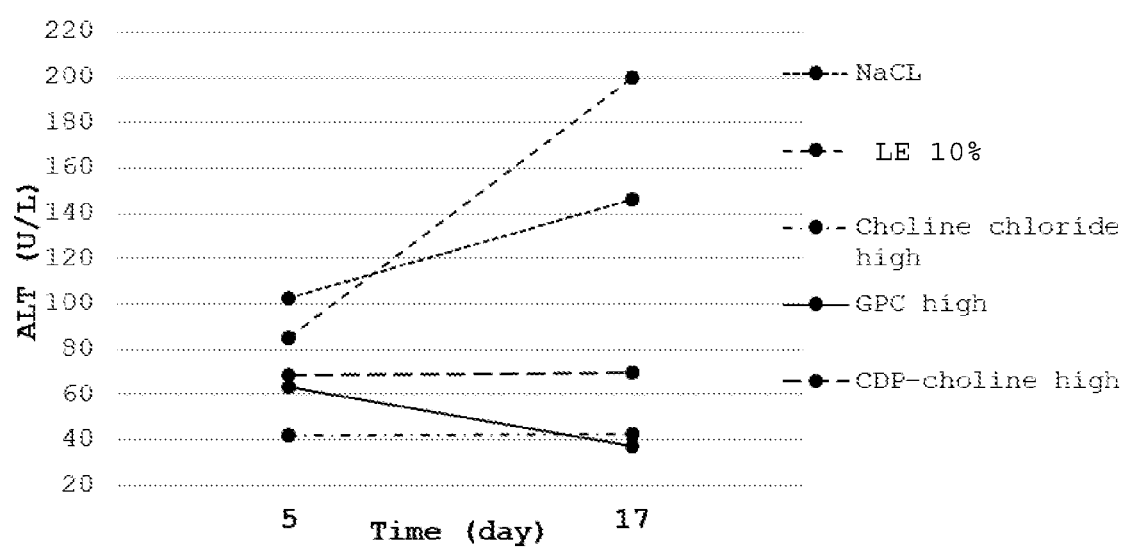
FIG. 1 depicts the development of the alanine aminotransferase (ALT) function in the animal study described in Example 1. Control groups received saline solution (NaCl) or lipid emulsion LE 10% only, whereas further groups received the same LE 10% lipid emulsion, however with three different choline sources, choline chloride, CDP-choline and GPC contained in the lipid emulsion. The expression "high" denotes a concentration of the choline derivative of 31 mmol/L in the LE 10% lipid emulsion. The graph show's that the drop of ALT activity from day 5 to day 17, demonstrating an improvement of the liver condition, is most pronounced when GPC is present in the lipid emulsion.

Certain embodiments described herein relate generally to the field of parenteral nutrition. More particularly, some embodiments described herein relate to lipid emulsions for parenteral administration, wherein the lipid emulsion comprises an aqueous phase and an oil phase and is present in the form of an oil-in-water emulsion. Other embodiments described herein relate to multi-chamber containers for parenteral administration, wherein the containers comprise said lipid emulsion in a first chamber and a carbohydrate formulation or amino acid formulation in a second chamber, optionally an amino acid in a third chamber when the second chamber contains a carbohydrate formulation, optionally a vitamin formulation or a trace element formulation in a fourth chamber, and optionally a trace element in a fifth chamber when the fourth chamber contains a vitamin formulation.

As used herein, the term "pediatric" refers to neonates, including premature (pre-term), full term, and post-mature neonates of up to one month of age; infants of between one month and one year of age; children of between one and up to 12 years of age, and adolescents of between 13 and up to 21 years of age. The term "adult" as used herein refers to persons of 22 years of age and older.

As used herein, the term "essentially free" may refer to a composition that contains no more than 5% of the specified component, for example, no more than 3%, no more than 2%, no more than 1%, no more than 0.5%, no more than 0.1%, no more than 0.05%, no more than 0.02%, no more than 0.01%, no more than 0.005%, no more than 0.002%, and/or no more than 0.001% of the specified component. For example, a lipid emulsion or composition that is "essentially free of EPA" may refer to a composition that contains no more than 5% EPA, such as no more than 3%, no more than 2%, no more than 1%, no more than 0.5%, no more than 0.1%, no more than 0.05%, no more than 0.02%, no more than 0.01%, no more than 0.005%, no more than 0.002%, and/or no more than 0.001% EPA.

The expressions "liver disease", "liver injury" and "liver damage" are interchangeably used herein. The expression refers to a condition of the liver which is defined by an increased alanine aminotransferase (ALT) activity, histologically determined vacuolation, as well as increase in the ratio of liver weight per body weight. Specifically, the expressions refer to hepatic steatosis which can be diagnosed by means of the above markers. More specifically, they refer to NAFLD, Even more specifically, they refer to NAFLD caused by choline deficiency, especially choline deficiency caused by long-term total parenteral nutrition.

The disclosure provides lipid formulations for parenteral administration comprising, as a choline source for patients in need thereof, glycerophosphocholine (GPC). Lipid formulations according to the invention which are intended for direct administration to a patient in need of parenteral nutrition contain GPC in a concentration of from 0.1 g to 15.0 g per liter of the lipid emulsion.

Pediatric patients generally require higher amounts of choline than adults. Lipid emulsions for direct administration to pediatric patients therefore can contain GPC in a range of from 2.0 g to 12.0 g per liter of lipid emulsion or from 4.0 g to 11.0 g per liter of lipid emulsion. For example, lipid emulsions for direct administration to pediatric patients contain GPC in a range of from 5.0 g to 12.0 g per liter of lipid emulsion, or in a range of from 4.0 g to 10.0 g per liter of lipid emulsion.

Adults, on average, require less choline. Lipid emulsions for direct administration to adult patients therefore can contain GPC in a range of from 0.1 g to 6.0 g per liter of lipid emulsion. For example, lipid emulsions for direct administration to adult patients contain GPC in a range of from 0.5 g to 5.0 g per liter of lipid emulsion, in a range of from 0.5 g to 4.0 g per liter of lipid emulsion, or in a range of from 0.5 g to 3.0 g per liter of lipid emulsion.

In the present invention, lipid emulsions, multi-chamber containers comprising same, and compositions reconstituted from such multi-chamber containers are disclosed which are characterized by the presence of GPC in the lipid emulsion or the reconstituted composition as described above. The composition of said lipid emulsions can otherwise vary over a broad range as concerns specific components and the sources thereof, as long as they can safely be used for intravenous administration to a patient in need of parenteral nutrition.

The lipid emulsions comprising GPC as disclosed above are used in the treatment of patients who require parenteral nutrition. Patients who can benefit from the lipid emulsions according to the present invention can be adult patients and pediatric patients, wherein the GPC concentration can be adjusted as disclosed before to address the higher choline needs of pediatric patients.

Patients, including said pediatric and adult patients, who can benefit from lipid emulsions according to the invention, are all patients who show signs of choline deficiency, including signs of hepatic steatosis, or are in danger to become choline deficient. Choline deficiency according to the invention may be caused, for example, by total parenteral nutrition with parenteral nutrition products which do not provide for the amounts of choline (equivalents) necessary to sustain an adequate intake (AI) tor adult men of about 550 mg/day (~8 mg/kg/day), tor adult women of about 425 mg/day (~6 mg/kg/day), for pediatrics od about 40 mg per day (~90 to 100 mg/kg/day).

The lipid emulsions according to the invention are also suitable for avoiding or treating choline deficiency in neonates, including pre-term and extremely pre-term children. As mentioned before, choline plays a central role in the development of said pediatric patients, as it is an essential structural component of cell membranes, the neurotransmitter acetylcholine and phospholipid synthesis, where it contributes to the synthesis of very low density lipoprotein necessary for formal triglyceride exportation from the liver. Given that choline is crucial for the synthesis of acetylcholine, which is the most relevant neurotransmitter in cholinergic cells, a deficiency in choline may be connected to such memory deficits. Choline is connected, especially in infants, with brain development. Choline deficiency further activates cellular apoptosis, which may contribute to a deficient cell repair mechanism. Importantly, choline deficiency leads to hepatic steatosis, which is especially of concern in infants, including pre-term babies, who require parenteral nutrition.

The present invention therefore provides for a lipid emulsion for preventing and/or treating hepatic steatosis in a patient, specifically in a patient who is on total parenteral nutrition, wherein the lipid emulsion comprises glycerophosphocholine according to the invention. However, the lipid emulsions of the invention or reconstituted compositions comprising same can be used in the parenteral nutrition of patients not suffering from hepatic steatosis, as the presence of GPC can avoid the occurrence of such liver damage.

As mentioned before, choline chloride and CDP-choline have already been used as choline derivatives for the supplementation of choline to patients. However, these compounds are not provided as a component of ready-to-use lipid emulsions for parenteral nutrition, which do not require the addition of choline chloride or CDP-choline to the formulation upon administration through the medical port or in a separate solution for intravenous application, thereby avoiding additional steps which carry the risk of wrong dosage or contamination. In fact, it was found, that it is difficult to stabilize said choline derivatives in parenteral nutrition solutions, including lipid emulsions (see Example 5).

In contrast, it was found during the work leading to the present invention, that GPC is not only more efficient in delivering choline to the patient in an effectively metabolizable form, but that it can further be stabilized in a lipid emulsion and further remains stable in a formulation which is reconstituted from a multi-chamber bag comprising such lipid emulsion in one of the chambers. Accordingly, the invention provides for a method of providing choline to a patient by parenteral nutrition as a component of a ready-to-use lipid emulsion or a reconstituted formulation comprising same, wherein the lipid emulsion comprises glycerophosphocholine according to the invention.

Lipid formulations such as disclosed herein are an emulsion of an oil phase, a water phase, and an emulsifier that makes the two phases miscible. In case of lipid emulsions, which are to be used as an injectable emulsion for parenteral nutrition, the emulsion must be an oil-in-water (o/w) emulsion. Tills means that the oil must reside in the internal (or dispersed) phase, while water is the external (or continuous) phase, as the emulsion must be miscible with blood. Lipid emulsion as disclosed herein must therefore also be substantially free of any suspended solids. Of course, the lipid emulsions may contain further components, including but not limited to, antioxidants, pH modifiers, isotonic agents, vitamins, trace elements and various combinations hereof. An overview over lipid emulsions, their composition and use is provided, for example, in Driscoll, Journal of Parenteral and Enteral Nutrition 2017, 41, 125-134. Further information on the use of lipid emulsions in parenteral nutrition of intensive care patients is provided, for example, in Calder et. al, Intensive Care Medicine, 2010, 36(5), 735-749.

The oil phase of the lipid emulsion generally includes polyunsaturated fatty acids, such as long-chain polyunsaturated fatty acids, which may be present as the free acid, as an ionized or salt form of the free acid, and/or in ester form. Suitable esters of the polyunsaturated fatty acids/long-chain polyunsaturated fatty acids include, but are not limited to, alkyl esters (e.g, methyl esters, ethyl esters, propyl esters, or combinations thereof) and triglyceride esters. In some cases, the long-chain polyunsaturated fatty acid has a structure $R((C=O)OR'$ wherein R is an alkenyl group having at least 17 carbon atoms, at least 19 carbon atoms, at least 21 carbon atoms, or at least 23 carbon atoms, and R' is absent, H, a counter ion, an alkyl group (e.g., methyl, ethyl, or propyl), or a glyceryl group (e.g., $R(C=O)OR'$ is a monoglyceride, a diglyceride, or a triglyceride). Polyunsaturated fatty acids for use in the lipid formulations disclosed herein include, but are not limited to, linoleic acid (LA), arachidonic acid (ARA), α-linolenic acid (ALA), eicosapentaenoic acid (EPA), docosahexaenoic acid (DHA), stearidonic acid (SDA), γ-linolenic acid (GLA), dihomo-γ-linolenic acid (DPA), and docosapentaenoic acid (DPA), particularly, DHA, ARA, and EPA, each of which may be present in free acid form, ionized or salt form, alkyl ester form, and/or triglyceride form. In some cases, the polyunsaturated fatty acids and/or long-chain fatty acids are present in triglyceride form.

Typically, the lipid formulation includes about 5% to about 35% by weight of an oil phase based on the total weight of the lipid emulsion. For example, the oil phase of the lipid emulsion is present in an amount of about 8% to 12%, of about 10% to about 20%, of about 10% to about 15%, of about 15% to about 20%, of about 12% to about 17%, of about 18% to 22% and/or about 20% by weight based on the total weight of the lipid formulation. The oil phase typically and preferably contains, in various amounts depending on the source of the oil, omega-3 fatty acids. The three types of omega-3 fatty acids involved in human metabolism are eicosapentaenoic acid (EPA) and docosahexaenoic acid (DHA), both of which are usually found in marine fish oils and α-linolenic acid (ALA), commonly found in plant oils.

The oil phase and its components can be derived from a single source or different sources (see, for example, Fell et al, Advances in Nutrition, 2015, 6(5), 600-610, Of the plant oils, currently used sources include, but are not United to, soybean and olive oil as well as coconut or palm kernel oil (medium-chain triglycerides (MCTs)). Another source are algae, including microalgae such as *Crypthecodinium cohnii* and *Schizochytrium* sp., which in some cases serve as the single source of the long-chain polyunsaturated fatty acid docosahexaenoic acid (DHA), Marine oil used in parenteral lipid emulsions is processed from oily fish primarily found in cold water and including but not limited to, herring shad and sardines. However, other marine organisms can be used as an oil source, such as, for example, krill, such as Antarctic krill (*Euphausia superbu* Dana). Krill oil, for example, provides for both EPA and DHA, in amounts of up to 35% w/w of the fatty acids. Krill oil as a component of lipid emulsions is considered to have anti-inflammatory properties due to the presence of DHA and EPA and is hypothesized to bind endotoxins (Bonaterra et al: Krill oil-in-water emulsions protects against lipopolysaccharides-induced proinflammatory activation of macrophages in vitro. Marine Drugs (2017), 15:74).

Many microbes including fungi, yeast and some bacteria have the ability to synthesize significant amounts of LC-PUFAs, mainly ARA (Sanaa et al., Journal of Advanced Research 11:3-13 (2018)). Relevant ARA-producers are, for example, the non-pathogenic fungi *Mortierella* spp. from which the species *M. alpina* 1S-4 and ATCC 32,222 produce ARA up to 70% of lipid s. [00104] In some cases, the oil phase includes a blend of oils derived from the microalgae *Schizochytrium* sp. and the fungi *Mortierella alpina*. The oils in such a blend include, but are not limited to, myristic acid (C14:0), palmitic acid (C16:0), palmitoleic acid (C16:1), stearic acid (C18:0), oleic acid (C18:1), linoleic acid (C18:2 n-6), gamma-linolenic acid (C18:3, n-6), alpha-linolenic acid (C18:3, n-3), arachidic acid (C20:0), ARA (C20:4, n-6), EPA (C20:5, n-3), behenic acid (C22:0), DPA (C22:5, n-3), DHA (C22:6, n-3), and lignoceric acid (C24:0). In some cases, the blend includes ARA, DHA, and EPA. The content of various fatty acids such as DHA, EPA, ARA, linoleic acid (LA) or alpha-linoleic acid (ALA) in oils from different sources are summarized, for example, in Fell et al., 2015.

In some embodiments of the invention, the oil phase of the lipid emulsion is essentially free of EPA and ARA, and either of EPA or ARA are added alone or in combination to the oil phase of the lipid emulsion. However, in some cases, when the oil phase already contains EPA and/or ARA, either of the said tatty acids is added alone or in combination with each other to increase the amount of either EPA and/or ARA in the lipid emulsion.

In some embodiments of the invention, the oil phase of the lipid emulsion therefore includes ARA. In one embodiment, the ARA is obtained from a fungus, preferably from *Mortierella alpina*. However, ARA can be obtained from various sources according to the present invention and is not limited to ARA derived from fungi. In some cases, ARA is present in a concentration of from 0.1 g to 15 g per 100 g of oil phase, for example, from 1.5 g to 7.5 g per 100 g of oil phase.

In some embodiments of the invention, the oil phase includes DHA and EPA in various ratios. In some cases, the oil phase contains more DHA than EPA, and in some cases DHA is present but the oil phase is essentially free of EPA. When both DHA and EPA are present, the ratio of DHA to EPA in the lipid emulsion is typically at least 10:1 (w/w), for example about 10:1 to about 1000:1 (w/w), about 20:1 to about 1000:1 (w/w), about 50:1 to about 1000:1 (w/w), about 100:1 to about 1000:1 (w/w), about 10:1 to about 200:1 (w/w), about 20:1 to about 150:1 (w/w), at least about 50:1 (w/w), at least about 100:1 (w/w), at least about 500:1 (w/w), and/or at least about 1000:1 (w/w).

In some cases, DHA is present in a concentration of from 0.25 g to 3.0 g per 100 g of oil phase. In some cases, DHA is present in the oil phase of the lipid emulsion in a concentration of from 1.5 g to 2.5 g per 100 g of oil phase. In some cases, the said DHA is present in triglyceride form or in ethyl ester form, preferably in triglyceride form.

An exemplary lipid emulsion according to the disclosure includes glycerophosphocholine (GPC) in a concentration of from 0.1 g to 2.0 g per liter of lipid emulsion. Such lipid emulsion can be used for direct parenteral administration. In certain embodiments, the lipid emulsion contains glycerophosphocholine (GPC) in a concentration of from 0.1 g to 2.0 g per liter of lipid emulsion and further contains a docosahexaenoic acid (DHA) in a concentration of from 0.1 g to 5.0 g per 100 g of oil phase. Such lipid emulsion may be essentially free of EPA or may contain low amounts of EPA, wherein the ratio between DHA and EPA is 10:1 to 1000:1 (w/v) or 10:1 to 200:1.

In certain embodiments, the lipid emulsion contains glycerophosphocholine (GPC) in a concentration of from 0.1 g to 2.0 g per liter of lipid emulsion, a docosahexaenoic acid (DHA) in a concentration of from 0.1 g to 5.0 g per 100 g of oil phase, and/or arachidonic acid (ARA) in a concentration of from 0.1 g to 15 g per 100 g of oil phase. In certain embodiments, the said lipid emulsion comprises DHA and ARA in a ratio of DHA to ARA in the lipid emulsion of from 10:1 to 1:5 (w/w). Such lipid emulsion may again be essentially free of EPA or may contain low amounts of EPA, wherein the ratio between DHA and EPA is 10:1 to 1000:1 (w/v) or 10:1 to 200:1.

The lipid emulsions disclosed herein in some cases include reduced levels of phytosterols. In such case, the oils used in the lipid emulsions have been depleted in phytosterols, typically by an amount of at least 25% of the total amount of phytosterols initially present in the oil, for example, at least 40%, at least 50%, at least 60%, and/or at least 75% depleted. In some cases, the lipid emulsions include 70 mg phytosterols or less per 100 g of oil phase, for example, about 15 mg to about 35 mg phytosterols per 100 g of oil phase, and/or about 25 mg phytosterols or less per 100 g of oil phase. Removal or depletion of phytosterols can be carried out by known processes, for example, short path distillation, active charcoal treatment following by filtration, supercritical $CO_2$ chromatography, or chromatographic purification.

The lipid emulsions disclosed herein may further include additional components, such as surfactants (also referred to as emulsifiers), co-surfactants, isotonic agents, pH adjusters, and antioxidants. Generally, surfactants are added to stabilize emulsions by reducing the interfacial tension between the oil phase and the aqueous phase. Surfactants typically include a hydrophobic part and a hydrophilic part, and the amount of surfactant/emulsifier included in the formulations is determined based on the amount that is needed to achieve a desired level of stabilization of the emulsion. Typically, the amount of surfactant in the lipid formulation is about 0.01% to about 3% by weight based on the total weight of the lipid formulation, for example, about 0.01% to about 2.5%, about 0.01% to about 2.3%, about 0.02% to about 2.2%, about 0.02% to about 2.1%, about 0.02% to about 2%, about 0.05% to about 1.8%, about 0.1% to about 1.6%, about 0.5% to about 1.5%, about 0.8% to about 1.4%, about 0.9% to about 1.3%, about 1% to about 1.2%, and/or about 1.2% by weight. Suitable surfactants and co-surfactants include surfactants that are approved for parenteral use, and include, but are not limited to, phospholipids (e.g., egg phosphatide and soy lecithin), oleate salts, and combinations thereof. Krill oil can also be used as an emulsifier in the lipid emulsion, wherein the lipid emulsion comprises about 0.5 to 2.2 wt % krill oil based on the total weight of the emulsion, and wherein the emulsion is free of egg yolk lecithin (US 2018/0000732 A1). Another exemplary surfactant is lecithin, including both natural and synthetic lecithin, such as lecithins derived from egg, corn or soybean or mixtures thereof. In some cases, lecithin is included in an amount of about 1.2% based on the total weight of the lipid formulation.

In some cases, the lipid emulsion formulation includes a co-surfactant. Typically, the amount of co-surfactant in the lipid formulation is less than the amount of surfactant, and typically the amount of co-surfactant in the formulation is about 0.001% to about 0.6% by weight based on the total weight of the lipid formulation, for example, about 0.001% to about 0.55%, about 0.001% to about 0.525%, about 0.001% to about 0.5%, about 0.005% to about 0.5%, about 0.01% to about 0.4%, about 0.02% to about 0.3%, about 0.03% to about 0.2%, about 0.04% to about 0.1%, and/or about 0.05% to about 0.08%. An exemplary co-surfactant is oleate, such as sodium oleate. In some cases, the lipid formulation includes lecithin and oleate as surfactant and co-surfactant, for example, an in amount of 1.2% lecithin and 0.03% oleate. In some cases, sodium oleate is included in an amount of about 0.03% by weight based on the total weight of the lipid formulation.

Isotonic agents can be added to the lipid emulsions to adjust the osmolarity of the lipid emulsion to a desired level, such as a physiologically acceptable level. Suitable isotonic agents include, but are not limited to, glycerol. Typically, the lipid emulsion formulation has an osmolarity of about 180 to about 300 milliosmols/liter, such as about 190 to about 280 milliosmols/liter, and/or about 200 to about 250 milliosmols/liter. In some cases, the lipid emulsion includes an isotonic agent in an amount of about 1% to about 10% by weight based on the total weight of the lipid formulation, such as about 1% to about 5%, about 1% to about 4%, and/or about 2% to about 3%. In some cases, the lipid emulsion formulation includes about 2% to about 3% by weight of glycerol.

pH modifiers can be added to the lipid emulsions to adjust the pH to a desired level, such as a physiologically acceptable pH for parenteral use. Suitable pH modifiers include, but are not limited to sodium hydroxide and hydrochloric acid. Typically, the lipid emulsion formulation has a pH of about 6 to about 9, such as about 6.1 to about 8.9, about 6.2 to about 8.8, about 6.3 to about 8.7, about 6.4 to about 8.6, about 6.5 to about 8.5, about 6.6 to about 8.4, about 6.7 to about 8.3, about 6.8 to about 8.2, about 6.9 to about 8.1, about 7 to about 8, about 7.1 to about 7.9, about 7.2 to about 7.8, about 7.3 to about 7.7, about 7.4 to about 7.6, about 7, about 7.5, and/or about 8.

The lipid formulations may further include antioxidants. Suitable antioxidants may be pharmaceutically acceptable antioxidants and include, but are not limited to, tocopherols (e.g., gamma tocopherol, delta, tocopherol, alpha tocopherol), ascorbyl palmitate, or combinations thereof. In some cases, the lipid emulsion formulation includes an antioxidant in an amount of about 0 to about 200 mg/L, for example, about 10 to about 200 mg/L, about 40 to about 150 mg/L, about 50 to about 120 mg/L, about 75 to about 100 mg/L antioxidant(s), such as vitamin E.

The aqueous (or water) phase of all intravenous lipid emulsions must conform to the pharmacopeial requirements that make it suitable for injection, that is, the water must be sterile water for injection.

Also included in the disclosure are lipid emulsions wherein the GPC is added, e.g, through a medical port, to a ready-to-use lipid emulsion or a reconstituted solution before administration to a patient. The GPC can be provided in the form of a suitable solution, for example in a vial or a suitable flexible or rigid container, or can be provided in lyophilized form, for example in a glass vial, wherein the lyophilized GPC is dissolved in a suitable solvent, before adding it to the lipid emulsion or reconstituted solution. GPC can be present as the single active component in such solution or lyophilisates for addition to a lipid emulsion or reconstituted solution, or can be present in combination with at least one further active component such as, for example, vitamins, trace elements, DHA, EPA and/or ARA. Therefore, according to another embodiment of the invention, a method of providing GPC to a patient is provided, wherein GPC is added to a ready-to-use lipid emulsion or a reconstituted solution from a MCB providing for formulations for parenteral nutrition before administration.

As mentioned before, the lipid emulsions can also be present in one of the chambers of a multi-chamber bag. The disclosure therefore also provides for a multi-chamber container for parenteral administration of nutritional formulations. For example, the container may be in the form of a bag having multiple compartments or chambers. The container, such as a bag, includes at least two chambers, but may also contain three, four, or five chambers, and in one preferred embodiment, two or three chambers. Suitable containers, including soft bags, typically are sterile, non-pyrogenic, single-use, and/or ready-to-use. The multi-chamber containers are particularly useful for holding a pediatric and/or neonatal parenteral nutrition product and generally provide a carbohydrate formulation as disclosed herein in the first chamber, an amino acid formulation as disclosed herein in a second chamber, and a lipid formulation as disclosed herein in a third chamber of the container.

The multi-chamber container, such as a three-chamber bag, may include vertical chambers. Suitable multi-chamber containers are disclosed in U.S. Patent Publication No. 2007/0092579. For example, the multi-chamber container may be configured as a bag that includes two or three adjacent chambers or compartments. If desired, frangible barriers or openable seals (e.g., peel seals or frangible seals) are used to separate the chambers of the multi-chamber container. Multi-chamber containers may also comprise three chambers for accommodating a lipid emulsion, a carbohydrate formulation and an amino acid formulation, and further comprise at least one, in certain embodiments two or three smaller chambers which contain, for example, vitamin formulations and/or trace element formulations. In one specific embodiment, the multi-chamber container of the invention has a first chamber containing the lipid emulsion according to the invention, a second chamber containing an amino acid formulation, a third chamber containing a carbohydrate formulation, a fourth chamber containing a vitamin formulation and a fifth chamber containing a trace element formulation.

The openable seals of said multi-chamber containers permit formulations to be separately stored and admixed/reconstituted just prior to administration thereby allowing storage in a single container of formulations which should not be stored as an admixture for an extended period of time. Opening of the seals allows communication between the chambers and mixing of the contents of the respective chambers. The outside seals of the multi-chamber container are strong seals that do not open under the fluid pressure supplied to open the weaker peel seals or frangible seals between the chambers. In some embodiments, the openable seals of the multi-chamber container may be designed to allow for the admixing or reconstitution of only selected chambers of the multi-chamber container, for example, the admixing of the lipid emulsion with the vitamin chamber and the amino acid chamber, if so desired.

The multi-chamber container may be provided with instructions explaining a desired order with which to open the peel seals, so that constituent fluids are mixed in a desired order. The unsealing strengths of the two or more peel seals may be varied to promote the opening of the seals in the desired order. For example, the unsealing strength of the peel seal to be opened first may be ⅓ to ½ of the unsealing strength required to open the peel seal to be opened second.

Where a lipid emulsion according to the invention is included into a multi-chamber bag, the GPC concentration in the lipid emulsion can be adapted as needed to arrive at the doses of GPC as disclosed before. However, lipid emulsions in a multi-chamber container may also comprise GPC in a concentration as disclosed before for the lipid emulsions.

As used herein, "reconstituted solution" refers to a solution for parenteral administration, which is generated by admixing the content of the chambers of a multi-chamber container before use.

Lipid emulsions contained in one chamber of a multi-chamber bag may contain GPC in a concentration of from 0.1 g to 15.0 g per liter. In some embodiments, the GPC concentration in such multi-chamber container may be from 1.0 g to 12 g per liter of lipid emulsion, from 1.0 g to 10.0 g per liter of lipid emulsion, from 2 g to 9.0 g per liter lipid emulsion, from 1.0 g to 5.0 g per liter of lipid emulsion, or from 2.0 g to 4.0 g per liter of lipid emulsion.

As mentioned above, Apical components of a multi-chamber container for providing formulations for parenteral nutrition are amino acid and/or carbohydrate formulations. The amino acid formulations include a sterile, aqueous solution of one or more amino acids and one or more electrolytes. Typically, amino acid formulations include about 2 g to about 10 grams of amino acids per 100 ml, of amino acid formulation, such as about 3 grams to about 9 grams and/or about 5 grams to about 7 grams per 100 mL of amino acid formulation. Typical amino acids which are included into amino acid formulations are, for example, isoleucine, leucine, valine, lysine, methionine, phenylalanine, threonine, tryptophan, arginine, histidine, alanine, aspartic acid, cysteine, glutamic acid, glycine, proline, serine, tyrosine, ornithine, and taurine. Further, the content of tyrosine can be increased by adding, for example, a glycyl-tyrosine dipeptide or acetyl-tyrosine (Ac-Tyr). Typically, however, the glycyl-tyrosine dipeptide has improved pharmacokinetics compared to Ac-Tyr, which is more rapidly eliminated by the kidney, resulting in diminished release of tyrosine in the blood.

The amino acid formulation may further include electrolytes such as sodium, potassium, calcium, magnesium, and/or phosphate ions. For example, the amino acid formulation can include from about 0.1 mmol to about 10 mmol of sodium (e.g., about 3.75 mmol to about 10 mmol of sodium), from about 0.1 mmol to about 10 mmol of potassium (e.g., about 3.75 mmol to about 6.90 mmol of potassium), from about 0.05 mmol to about 1.0 mmol of magnesium (e.g., about 0.05 mmol to about 0.11 mmol and/or about 0.38 mmol to about 0.65 mmol of magnesium), from about 0.1 mmol to about 10 mmol of calcium (e.g., about 1.13 mmol to about 5.10 mmol of calcium), from about 0.1 mmol to about 10 mmol of phosphate (e.g., about 0.94 mmol to about 5.10 mmol of phosphate) and not more than 10 mmol of chloride (e.g., not more than 5.6 mmol of chloride) per 100 mL of amino acid formulation. When calcium and phosphorus are present together in the same heat-sterilized solution, insoluble calcium phosphate precipitation can occur. Using an organic salt of phosphorus such as sodium glycerophosphate $5 \cdot H_2O$ or calcium glycerophosphate, calcium and phosphate amounts may be increased without solubility issues and without providing excess sodium or chloride. In the amino acid formulation, sodium may be provided in the form of sodium chloride, calcium may be provided in the form of calcium chloride $2 \cdot H_2O$ or calcium gluconate, magnesium may be provided in the form of magnesium acetate $4 \cdot H_2O$ or magnesium chloride, and potassium may be provided in the form of potassium acetate.

The carbohydrate formulations provide a supply of calories, typically in the form of glucose.

In particular, the carbohydrate formulation provides an amount of carbohydrate sufficient to avoid adverse effects such as hyperglycemia that has been observed inpatients receiving parenteral nutrition. Typically, the carbohydrate formulation includes about 20 to 50 grams of glucose per 100 mL of carbohydrate formulation.

The lipid emulsions of the invention can be prepared according to generally known processes (see, for example, Hippalgaonkar et al, AAPS PharmSciTech 2010, 11(4), 1526-1540). Generally, water soluble and oil-soluble ingredients are dissolved in the aqueous phase and oil phase, respectively. Accordingly, GPC is dissolved in the aqueous phase. Emulsifiers, such as phosphatides, can be dispersed in either oil or aqueous phase. Both phases are adequately heated and stirred to disperse or dissolve the ingredients. The lipid phase is then generally added to the aqueous phase under controlled temperature and agitation (using high-shear mixers) to form a homogenously dispersed coarse or pre-emulsion. Pre-emulsions with a droplet size smaller than 20 μm generally produces unimodal and physically stable fine emulsions. The pre-emulsion is then homogenized (using a microfluidizer or a high-pressure homogenizer) at optimized pressure, temperature, and number of cycles to further reduce the droplet size and form a fine emulsion. Factors such as type and concentration of oil phase and surfactants, operating temperature, pressure, number of cycles, etc. can influence the mean droplet size during high-pressure homogenization and micro fluidization. Throughout the shelf-life of an emulsion, the mean droplet size and PFAT5 (volume-weighted percentage of tat globules ≥5 μm) of an injectable fine emulsion should be ≤500 nm and ≤0.05%, respectively. The pH of the resulting fine emulsion is then adjusted to the desired value and the emulsion is filtered through 1-5 μm filters. The fine emulsions are then transferred into suitable containers. Plastic containers which are permeable to oxygen and/or contain oil-soluble plasticizers and usually avoided. The entire process (filtration/coarse and fine emulsion preparation) is usually carried out under nitrogen atmosphere whenever possible and especially in cases where the excipients and specific components of the lipid emulsion are sensitive to oxidation. Sterilization of the lipid formulations can be achieved by terminal heat sterilization or by aseptic filtration. Terminal sterilization generally provides greater assurance of sterility of the final product. However, if the components of the emulsions are heat labile, sterile filtration can be used. Sterilization by filtration requires the emulsion droplet size to be below 200 nm. Alternatively, aseptic processing may be employed. However, this process is relatively equipment and labor intensive and requires additional process validation data and justification during regulatory submissions.

Accordingly, lipid emulsions according to the invention can be prepared by the following steps comprising
  (a) Separately heating up the oil phase and the aqueous phase to a temperature of from about 70° C. to about 80° C. under agitation;
  (b) Adding glycerophosphocholine to the aqueous phase;
  (c) Preparing the pre-emulsion by transferring the oil phase to the aqueous phase under agitation;
  (d) Homogenizing the pre-emulsion at a temperature of from about 40° C. to 60° C. under pressure;
  (e) Optionally adding water to adjust the required volume and concentrations,
  (f) Optionally adjusting the pH to a range of from about 7.8 to 8.8; and
  (g) Optionally sterilizing the lipid emulsion.

Sterilization can be done by methods known in the art, such as, for example, by heat. Usually, steps (a) through (d) will be performed in the presence of an inert gas, such as $N_2$, for avoiding any oxidation reactions. The pressure used for homogenization of the pre-emulsion can vary over a broad range. Generally, it will be in a range of from 100 to 1300 bar, from 200 to 1000 bar, from 300 to 800 bar, or from 400 to 1100 bar.

As discussed before, the invention relates to lipid emulsions and compositions comprising same for avoiding and/or treating hepatic steatosis. Hepatic steatosis is defined as intrahepatic fat of at least 5% of liver weight. Simple accumulation of triacylglycerols in the liver could be hepatoprotective; however, prolonged hepatic lipid storage may lead to liver metabolic dysfunction, inflammation, and advanced forms of nonalcoholic fatty liver disease (NAFLD). NAFLD includes a spectrum of disease from simple steatosis to nonalcoholic steatohepatitis (NASH), which can progress to cirrhosis and hepatocellular carcinoma. Histologically, NASH is defined by the presence of macrovesicular steatosis, lobular inflammation, and hepatocellular ballooning (Kneeman, Secondary Causes of nonalcoholic fatty liver disease, Therap Adv Gastroenterol 2012; 5: 199-207). Long-term total parenteral nutrition (TPN) can be one of many causes for NAFLD. TPN may lead to the depletion of carnitine, a compound necessary for the transfer of free fatty acids from the hepatic cytoplasm into the mitochondria for beta-oxidation. As mentioned before, the cytosolic concentration of choline also decreases, promoting lipid storage in hepatocytes. Such lipid storage is connected to the fact that predominant histologic findings are steatosis, intrahepatic cholestasis, and ductular reduplication. Accordingly, the effect of choline supplementation in TPN can also be determined by validating the histological features of the liver. Such histological analysis allows assessment of the degree of steatosis by analyzing the extent of vacuolation. Example 3 provides for the results of such histopathological investigations done in an animal study. It is shown there that liver damage due to methionine and choline deficient diet followed by parenteral nutrition can be effectively addressed by the presence of glycerophosphocholine in the PN solution. It also provides for the evidence that GPC provides for a significantly better effect than other choline derivatives, specifically choline chloride and CDP-choline. The additional presence of DHA and ARA seem to have an additional, synergistic benefit.

Figure 2:
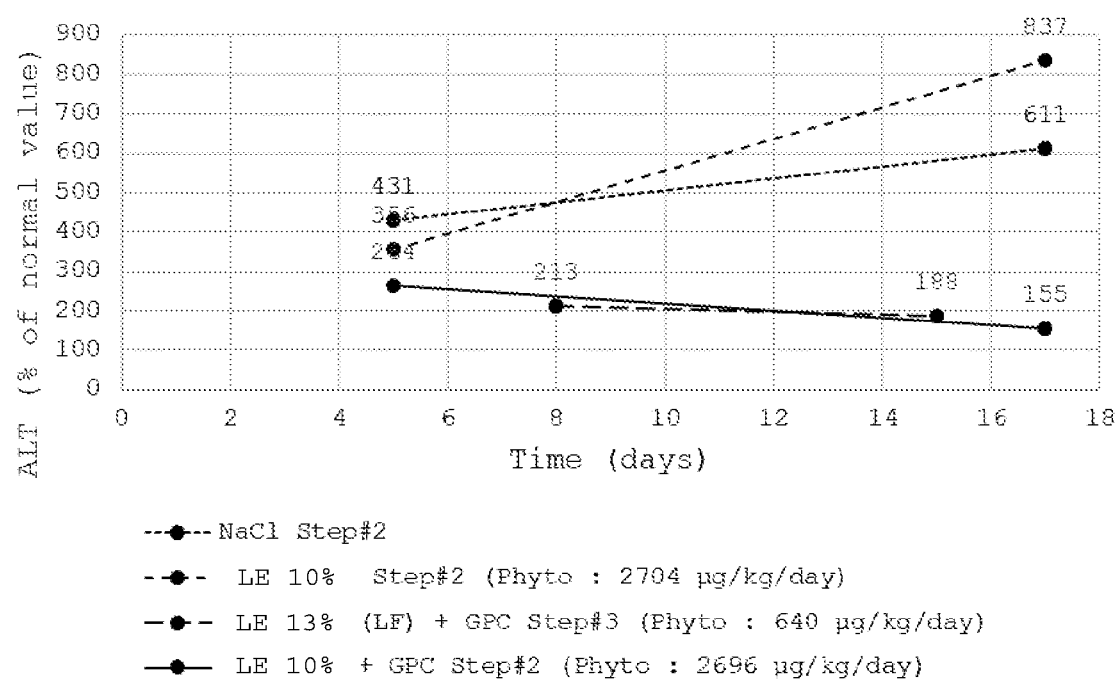
FIG. 2 shows the development of the alanine aminotransferase activity in percent of the normal value for plasma in an animal study as described in Example 1 (Step #3). The animals tested received either saline solution or LE 10% lipid emulsion ("LE 10%") only, wherein the lipid emulsion contained normal amounts of phytosterol ("Phyto") but no GPC. Another lipid emulsion, containing also LE 10% and comparable amounts of phytosterol, further contained GPC in a concentration of 40 mmol/L ("LE 10%+GPC Step #2"). A third composition was again consisting of a lipid emulsion (LE 13%) with GPC added at a concentration of 40 mmol/L and a reduced phytosterol content (phytosterol doses are given in FIG. 2).

Serum alanine aminotransferase (ALT) assays are the most common laboratory tests for the detection of liver diseases. Because the enzyme concentration in a population forms a continuous distribution, the cut-off concentration that discriminates between healthy and diseased livers is not clearly defined. However, the upper normal limit of serum alanine aminotransferase is set on average at 40 IU/l, ranging from 30-50 IU/1 (Kim et al. BMJ 2004, 328:983). Said upper limit is used as a normal serum alanine aminotransferase (referred herein also as "aminotransferase" or "ALT") concentration in the context of the present invention. Kim et al. also describe that the association between the aminotransferase concentration and mortality from liver disease is significant. Therefore, serum aminotransferase concentration was used in the context of the present invention to determine the efficacy of glycerophosphocholine for the treatment of liver damage which can be caused, for example, by parenteral nutrition in comparison to lipid emulsion not containing any choline, but also in comparison with other choline sources, including choline chloride and CDP-choline. FIGS. 1 and 2 demonstrate the significantly better effect of GPC on lowering ALT concentrations.

ALT activity is determined by a modification recommended by the International Federation of Clinical Chemistry (IFCC), see also Example 2. ALT catalyzes the reaction of alpha-ketoglutarate with L-alanine to form L-glutamate and pyruvate. Under the action of LDH, pyruvate converts to lactate, and NADH is converted to NAD. The decrease in absorbance of NADH, measured at 340 nm (secondary wavelength is 700 nm), is directly proportional to the serum activity of ALT. It is a kinetic reaction. In general, serum is used for analysis. The serum is separated from the cells within 2 hours of collection and stored at −70° C. until assayed, Monitoring the ALT activity over time in an animal model is used herein as one straightforward and conclusive way to determine the efficacy of GPC in treating liver disease, specifically liver damage caused by a choline-deficient diet (Examples 1 and 2, FIGS. 1 and 2), Plasma-free choline concentration can be determined by high-pressure liquid chromatography (HPLC) and gas chromatography-mass spectrometry according to protocols known in the art (Pomfret et. al.: Measurement of choline and choline metabolite concentrations using high pressure liquid chromatography and gas chromatography-mass spectrometry. Anal Biochem. 1989; 180: 85-90).

Methods of depleting phytosterol from an oil, specifically from a plant derived oil, such as olive or soybean oils, are known. For example, phytosterols can be removed as described in Ostlund et al, Am J Clin Nutr 2002, 75, 1000-1004, or as described in U.S. Pat. No. 6,303,803 B1.

EXAMPLES

Example 1: Animal Model

Animal studies were performed in order to identify and confirm the most effective choline derivative for use in parenteral nutrition solutions, specifically in lipid emulsions, for avoiding and/or treating and ameliorating liver damage, specifically liver steatosis. The study further served to identify any potential metabolic interactions between the choline derivate which was found to be the most effective and polyunsaturated fatty acids, specifically of DHA and ARA.

The effects of GPC as well as of the combination of DHA, ARA and GPC were investigated in a sick animal model, wherein male Sprague-Dawley rats with steatosis, induced by choline and methionine deficient (MCD) diet (S SNIFF MCD pelleted choline/methionine deficient diet (SSNIFF Spezialdiäten GmbH, Soest, Germany, Product No. E15653-94)) were kept on parenteral nutrition. Steatosis was confirmed in the respective groups by histopathology (Example 3).

Parenteral nutrition started after 14 days under MCD diet. First measurements were done after 5 days of parenteral nutrition, followed by measurements after 9 and 17 days. The daily lipid uptake was 2.31 g/kg/d. The rats were split into several groups as set forth below in Table I.

Two groups served as control groups, wherein a first group was treated with saline solution (0.90% w/v of NaCl in water for injection). A second group received a lipid emulsion ("LE 10%") containing refined olive oil (80.0 g/L) and refined soybean oil (20.0 g/L) in water for injection, pH 6-8; LE 10% further contained egg lecithin (6.0 g/L), glycerol (11.25 g/L) and sodium oleate (0.15 g/L). LE 10% contained 100 g/L lipids. In certain experiments the lipid emulsion "LE" was used in different concentrations, for example as "LE 13%", or "LE 20%" which indicates that the above concentrations were accordingly higher.

Various choline derivatives selected from the group consisting of choline chloride, glycerophosphocholine (GPC) and cytidine diphosphate-choline (CDP-choline) were added in two concentrations (low/high) to LE 10%, respectively, see Table I (Step #2). "Low" refers to a concentration of 15 mmol/L lipid emulsion, "high" refers to a concentration of 31 mmol/L of lipid emulsion. Choline chloride (2-Hydroxyethyl)trimethylammonium chloride). Pharmaceutical Secondary Standard, was purchased from Sigma-Aldrich (Merck KGaA, Germany). CDP-choline (prepared by fermentation) was from TCI Europe N.V. (Antwerp, Belgium). Glycerophosphocholine, prepared from egg phosphatide by saponification, was supplied by Lipoid GmbH, Germany. DHA (from algae, *Schizochytrium* sp.) and ARA (from fungi, *Mortierella alpina*) were purchased from BASF AG, Germany, Vitamin E was purchased from ADM (IL, U.S.A.)

The choline derivative supplemented "LE" lipid emulsions were prepared as follows. In a first step, raw phases are heated up. In case of the oil phase, soybean and olive oils and egg phosphatide as well as DHA and ARA oils and vitamin E in case of Step #3 experiments are heated in an inox beaker to 75° C. under $N_2$ protection while continuously agitating using an Ultra Turrax. The aqueous phase was prepared by mixing glycerol, sodium oleate and Milli-Q water and constantly heated in an inox beaker to about 75° C. under $N_2$ protection. Where needed, the choline derivative is added under constant agitation. In a second step, the pre-emulsion is prepared by adding the oily phase to the aqueous phase using a peristaltic pump under continuous agitation and then transferred to a high shear inline disperser (e.g. Dispax Reactor® DR). The receiving vessel is closed and flushed with nitrogen. In a third step the pre-emulsion is homogenized by passing it several times through a high-pressure homogenizer at 600 bar and a temperature of about 50° C., under a $N_2$ atmosphere.

The emulsion is then adjusted to the required volume (2 L) with Milli-Q water and cooled down to a temperature of approximately 18 to 28° C., preferably 20° C. to 25° C. The pH is adjusted to a range of from 7.8 to 8.8, preferably to about 8.3 to 8.8 with 0.1 N NaOH. The emulsion is filtered with a 4.5 μm filter and transferred in 100 mL bags, which are then over-pouched, making use of an oxygen absorber/indicator, for later use. The lipid emulsion is then autoclaved at 121° C. to achieve a F0 of at least 15 minutes.

TABLE I

Study Groups and Experimental Setup: Standard "LE" lipid emulsion was used for the experiments wherein certain amounts of a choline source were added to the lipid emulsion. This test setup which is focused on the effect of GPC as such is otherwise designated as "Step#2")

| Group | Lipid Emulsion/ Solution | Choline Equivalent [mmol/L] | Dose [mmol/ kg/day] |
|---|---|---|---|
| Control 1 | Saline Solution | — | — |
| Control 2 | LE 10% | — | — |
| Efficacy | LE 10% | Choline Chloride [15] | 0.38* |
|  |  | Choline Chloride [31] | 0.77* |
| Efficacy | LE 10% | Glycerophosphocholine [15] | 0.38* |
|  |  | Glycerophosphocholine [31] | 0.77* |
| Efficacy | LE 10% | CDP-choline [15] | 0.38* |
|  |  | CDP-choline [31] | 0.77* |

In further tests, the LE lipid emulsion according to the one described above was used. However, the content of phytosterol was reduced as indicated in the respective experiments. The phytosterol depleted LE lipid emulsion was supplemented for the tests with vitamin E in a concentration of 40 μg/ml of lipid emulsion, see Table II. In addition, DHA was contained in the lipid emulsion in a final concentration of about 2 to 3 g/L. ARA was contained in the lipid emulsion in a final concentration of about 5 to 6 g/L. The concentration of GPC was slightly higher here in comparison to Step #2 (40 mmol/L), but the dose was kept to 0.77 mmol/kg/d as shown in Table I. This test setup, which also takes into consideration synergistic effects of DHA and ARA in the formulation together with GPC was labeled herein as "Step #3".

TABLE II

Study Groups and Experimental Setup: Phytosterol depleted "LE" lipid emulsion as described above was used for experiments, wherein GPC as well as DHA and ARA were added as indicated. This test setup is otherwise designated as "Step#3").

| Group | Lipid emulsion/Solution | Choline Source [mmol/L] |
|---|---|---|
| Control | Saline solution | — |
| Control | LE 13%, phytosterol depleted, +DHA and ARA + vitamin E supplementation (40 μg/mL LE) | none |

TABLE II-continued

Study Groups and Experimental Setup: Phytosterol depleted "LE" lipid emulsion as described above was used for experiments, wherein GPC as well as DHA and ARA were added as indicated. This test setup is otherwise designated as "Step#3").

| Group | Lipid emulsion/Solution | Choline Source [mmol/L] |
|---|---|---|
| Efficacy | LE 13%, phytosterol depleted, +vitamin E supplementation (40 µg/mL LE) | Glycerophosphocholine [40 mmol/L] |
| Efficacy | LE 13%, phytosterol depleted + DHA and ARA + vitamin E supplementation (40 µg/mL LE) | Glycerophosphocholine [40 mmol/L] |

Example 2: Aminotransferase (ALT) Development

For assessing the effect of GPC on the liver status of the animals tested as described in Example 1, the aminotransferase (ALT) activity in the plasma of tested animals was tested after 5 and 17 days of parenteral nutrition both in a Step #2 and Step #3 setup. As described before, liver damage (cholestasis) may be determined by increased aminotransferase levels. ALT activity was determined with an ADVIA 1800 blood biochemistry analyzer/IFCC modified (Siemens) according to standard protocols such as described before.

In order to summarize the results of the experiments, FIG. 1 show's the development of ALT activity in the tested rats. As can be seen there, there is an expected increase in ALT activity upon parenteral nutrition over 17 days with LE 10%. In comparison, ALT activity does not increase in study groups where a choline source is present in the lipid emulsion. However, the effect is most notable in the presence of GPC, where a clear drop in ALT activity can be determined. In contrast, choline chloride and CDP-choline rather provide for a stable situation where ALT activity neither significantly increases or decreases. Notably, phosphatidylcholine which is contained in LE lipid emulsion(s) does not seem to have any effect, confirming that choline cannot make use of the choline pro vided in the form of phosphorylcholine in lipid emulsions.

After having identified GPC as a surprisingly effective choline derivative for the reduction of ALT activity and thus liver damage, another experiment focused on the synergy between GPC and the PUFAs DHA and ARA.

FIG. 2 summarizes the results for ALT activity in terms of the change in activity of the normal value. The test includes one experiment with a composition wherein the phytosterol content of the lipid emulsion was reduced as indicated in FIG. 2 according to the Step #3 setup. The results also demonstrate that both the saline solution and lipid emulsion ("LE") without choline source and normal phytosterol content lead to an increase in ALT activity, evidencing a progressive deterioration of the liver. In contrast, both lipid emulsions with GPC (40 mmol/L), irrespective of the phytosterol content, result in a significant decrease of ALT activity. Phytosterol doses are shown in FIG. 2. Phytosterol was contained in the LE 13% lipid emulsion in a concentration of from 40 µg/mL to 120 µg/L. Notably, phosphatidylcholine which is contained in the lipid emulsion(s) used here does not seem to have any effect, confirming that the body cannot make use of the choline provided in the form of phosphorylcholine in lipid emulsions.

Example 3: Determination of Histopathological Grades

Example 3.1: Preparation of Histological Slides

A part of the liver was preserved in buffered formalin, the infusion sites and the sampled macroscopic lesions were trimmed according to the RITA guidelines, where applicable (Ruehl-Fehlert et al, Exp Toxic Pathol 2003, 55, 91-106), embedded in paraffin wax, sectioned at a thickness of approximately four microns and stained with hematoxylineosin. The frozen liver sample was cryosectioned in slides of approximately five microns and stained by Oil Red O.

Tissue processing was performed at Citoxlab, France.

Example 3.2: Microscopic Examination

A microscopic examination was performed on both slides (hematoxylin eosin and Oil Red O) of the liver, the infusion sites and the macroscopic lesions from all animals of the study. Peer review was performed on at least 30% of the animals from the high-dose group and on an adequate number of slides from identified target organs to confirm that findings recorded by the Study Pathologist were consistent and accurate. After completion of the pathology peer review, all tissue slides were returned to Citoxlab France for archiving. During microscopic examinations, representative photographs were made at the discretion of the pathologist.

Example 3.3: Mean Histology Vacuolation

Liver samples taken after 8 and 15 days, respectively, were examined as described above and assigned to five grades of hepatocellular vacuolation. Vacuolation was generally diffuse and affected all regions for Grade 5. Periportal areas were lesser affected and the vacuoles were smaller in size for lower grades. Grades have been assigned according to the following definition:

GRADE 1=Minimal/very few/very small vacuoles, scattered.

GRADE 2=Slight/few/small vacuoles, centrilobular to midzonal.

GRADE 3=Moderate/moderate number/moderate size vacuoles, centrilobular to midzonal.

GRADE 4=Marked/many/large vacuoles, centrilobular to periporta.

GRADE 5=Severe/many/large vacuoles, diffuse, all liver regions affected.

Exemplary photographs for each Grade are shown in FIG. 5. The histological slides shown are stained with hematoxylin-eosin (HE).

After 8 days, the administration of saline solution results in four of four animals showing signs of liver damage in terms of vacuolation according to Grade 5 (see Table III). Parenteral nutrition with LE 13% in the presence of DHA and ARA already generates a positive effect on liver histopathology. Out of five animals, two still show Grade 5 vacuolation. However, three of the five animals' livers can be assigned to Grade 4. In the presence of GPC additional to DHA and ARA, the vacuolation of the liver is even more improved. Only one of five animals shows Grade 5 signs of liver damage, whereas another two rats show Grade 4 symptoms and two Grade 3 symptoms. Finally, if only GPC is added to the lipid emulsion, none of the five rats shows Grade 5 damage of the liver. Three show Grade 4, one shows Grade 3 and one even shows Grade 2vacuolation.

TABLE III

Microscopic changes of the liver after 8 days
Relevant microscopic changes in the liver on Day 8

| | Group | | | |
|---|---|---|---|---|
| | 1 | 2 | 3 | 4 |
| | | Treatment | | |
| | Saline solution | LE 13% + DHA + ARA | LE 13% + DHA + ARA + GPC | LE 13% + GPC |
| No. animals | 4 | 5 | 5 | 5 |
| | | Vacuolation; hepatocellular | | |
| Grade 2 | — | — | — | 1 |
| Grade 3 | — | — | 2 | 1 |
| Grade 4 | — | 3 | 2 | 3 |
| Grade 5 | 4 | — | 1 | — |

Figure 3A:
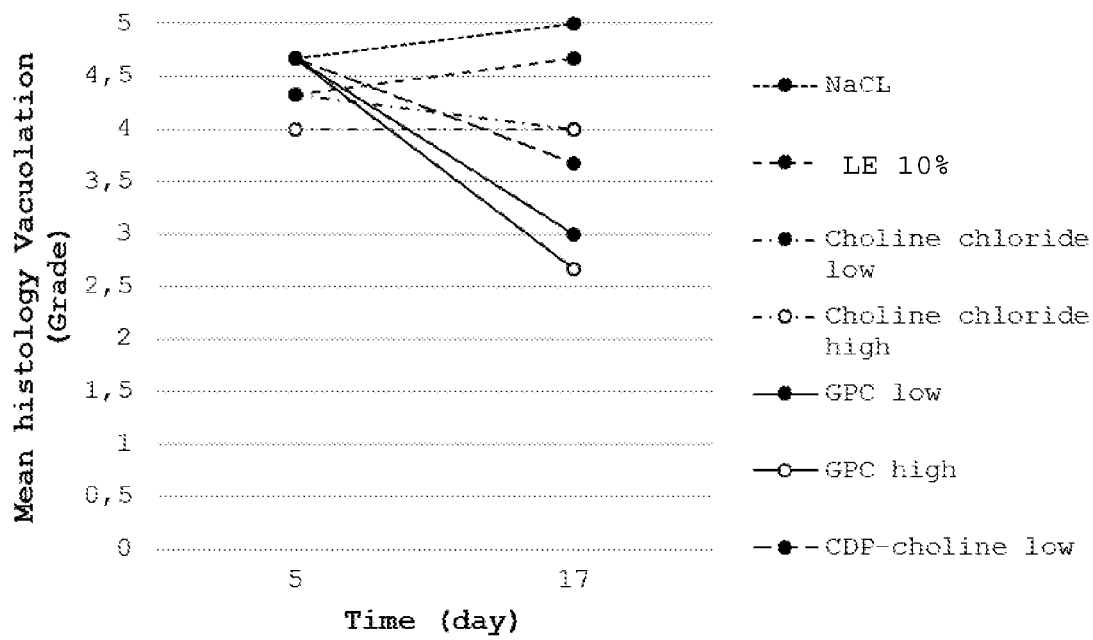
FIG. 3A and FIG. 3B represent the results of the animal study as described in Example 1 and the histopathological evaluation of the livers of animals that had been subjected to parenteral nutrition with saline solution, LE 10% lipid emulsion, and LE 10% lipid emulsions supplemented with choline chloride, CDP-choline and GPC, respectively (FIG. 3A).
Figure 3B:
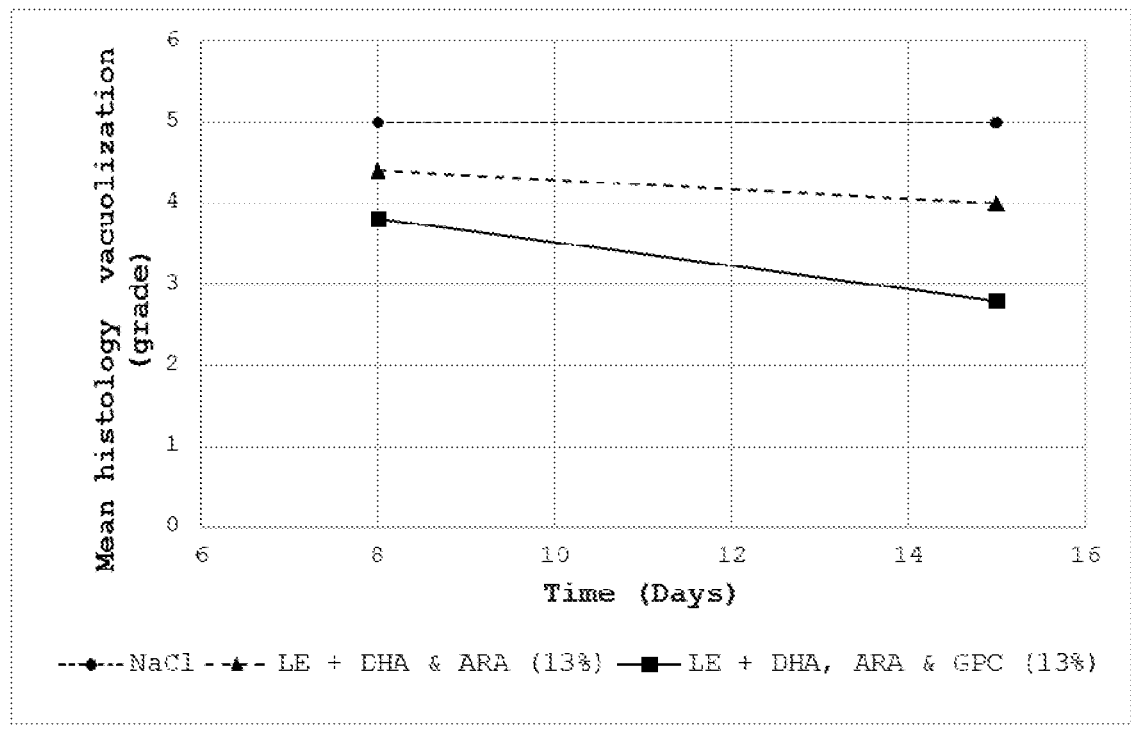

After 15 days into parenteral nutrition, the above effect was even more pronounced. Whereas the liver condition of those animals receiving saline solution remained as critical as could be expected, the presence of GPC in the lipid emulsion as well as the presence of all of DHA, ARA and GPC lead to a clear and significant improvement of the liver status of the animal. After 15 days, it becomes evident also that the presence of DHA and ARA within a certain concentration range in addition to GPC even lead to synergistically improved results. FIG. 3B summarizes the effects of DHA, ARA and GPC on the development of liver vacuolation, in terms of the above defined grades. The graph shows a significant amelioration of the liver condition in the presence of all DHA, ARA and GPC, wherein GPC seems to have an additional, surprising impact in the already beneficial presence of DHA and ARA in the lipid emulsion.

Identical histopathological tests were performed for comparing the effect of choline derivatives alone, i.e. in the absence of DHA and ARA. FIG. 3A summarizes the result of the histopathological examination of the livers of the animal study group. The effects of GPC are significantly better, both in at a high (31 mmol/L) and low (15 mmol/L) GPC concentration. CDP-choline (low concentration, 15 mmol/L) also had an effect. No grades could be assigned to the CDP-choline group with a high concentration (31 mmol/L). The groups which had received choline chloride as part of the lipid emulsion (high and low concentration) fared better than those with only saline or lipid emulsion without any choline derivative. However, the liver damage could not be addressed with said choline chloride supplemented lipid emulsions to any relevant extent.

TABLE IV

Microscopic changes of the liver after 15 days
Relevant microscopic changes in the liver on Day 15

| | Group | | | |
|---|---|---|---|---|
| | 1 | 2 | 3 | 4 |
| | | Treatment | | |
| | Saline solution | LE 13% + DHA + ARA | LE 13% + DHA + ARA + GPC | LE 13% + GPC |
| No. animals | 5 | 5 | 5 | 5 |
| | | Vacuolation; hepatocellular | | |
| Grade 2 | — | 1 | 1 | 2 |
| Grade 3 | — | — | 4 | 2 |
| Grade 4 | — | 2 | — | 1 |
| Grade 5 | 5 | 2 | — | — |

Example 4: Development of Liver to Body Weight

Figure 4:
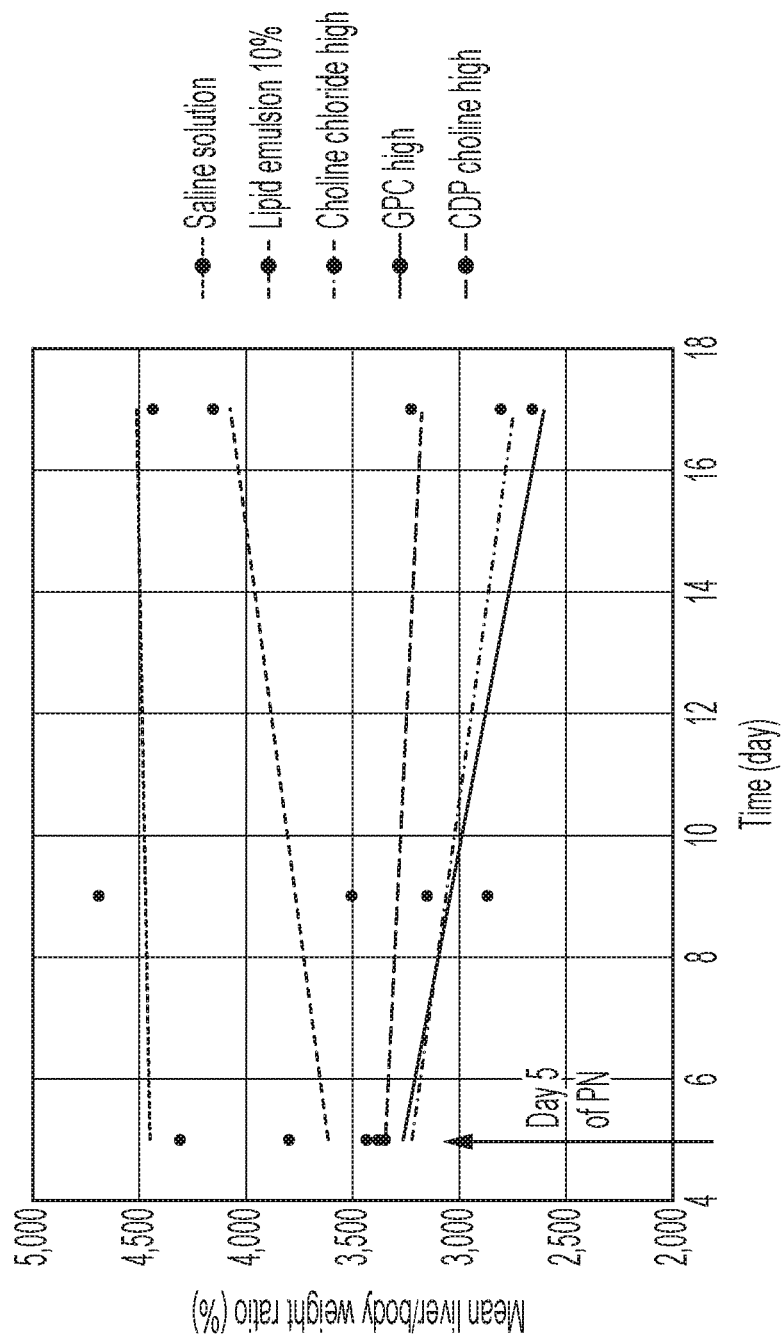
FIG. 4 represents the results of the animal study as described in Example 1, wherein the influence of the parenteral administration of various lipid emulsions was determined based on the ratio of liver weight and body weight in percent. The study animals were treated with either saline solution, LE 10% lipid emulsion ("Lipid emulsion 10%") without any choline derivative, and the same LE 10% lipid emulsion further containing 31 mmol/L of a choline derivative as shown. The expression "high" refers to a choline derivative concentration in the lipid emulsion of 31 mmol/L.
Figure 5A:
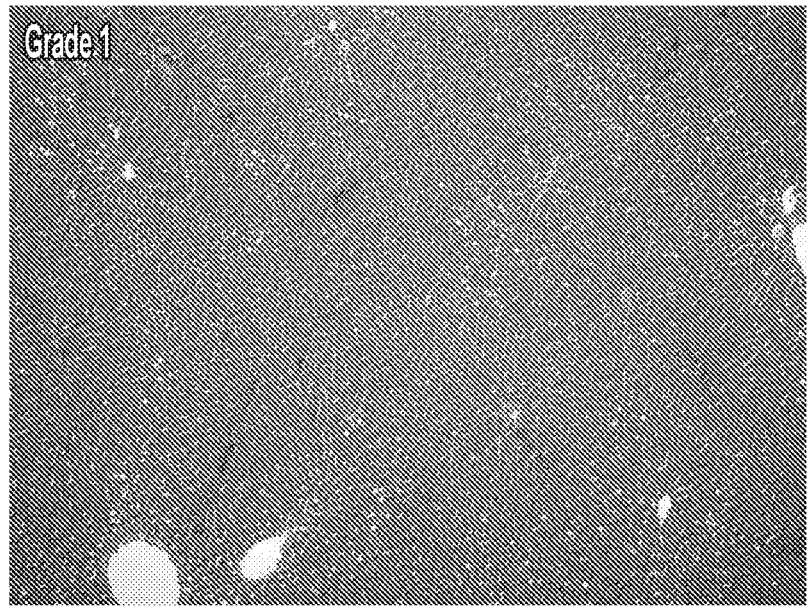
FIG. 5A: GRADE 1=Minimal/very few/very small vacuoles, scattered.
Figure 5B:
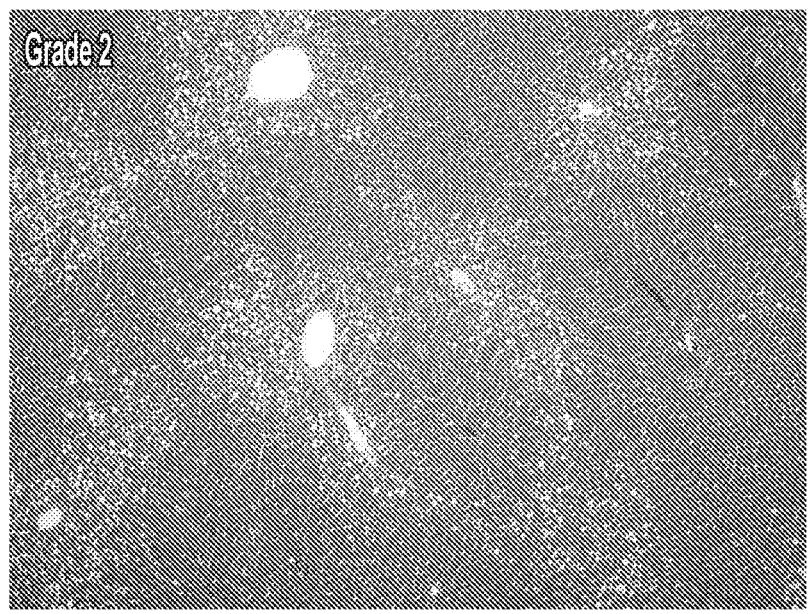
FIG. 5B: GRADE 2=Slight/few/small vacuoles, centrilobular to midzonal.
Figure 5C:
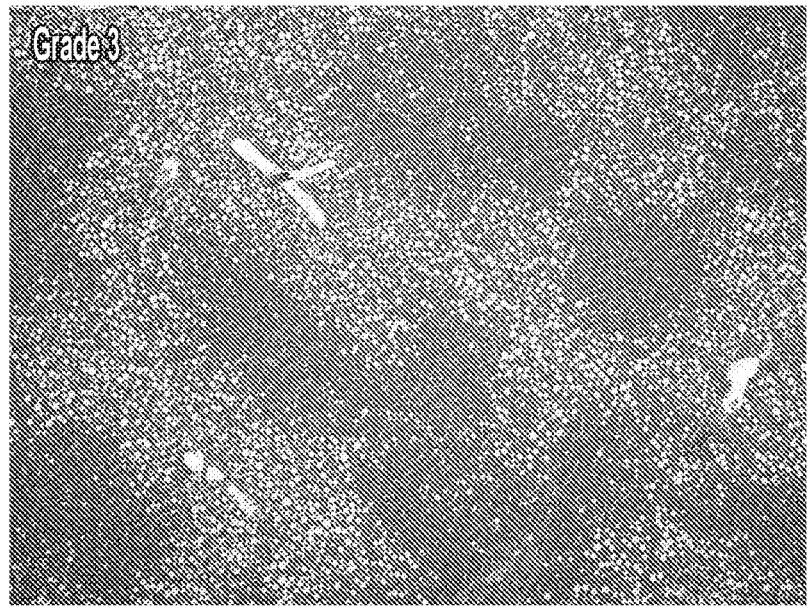
FIG. 5C: GRADE 3=Moderate/moderate number/moderate size vacuoles, centrilobular to midzonal.
Figure 5D:
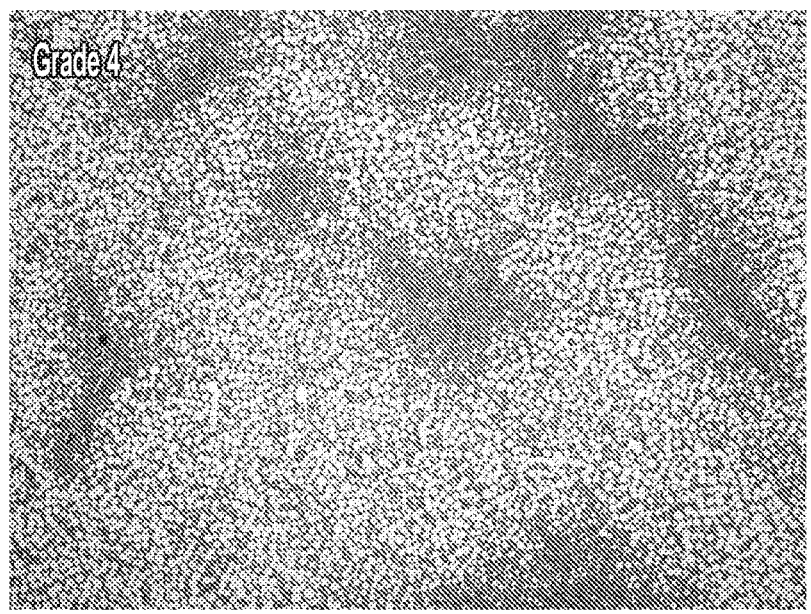
FIG. 5D: GRADE 4=Marked/many/large vacuoles, centrilobular to periportal.
Figure 5E:
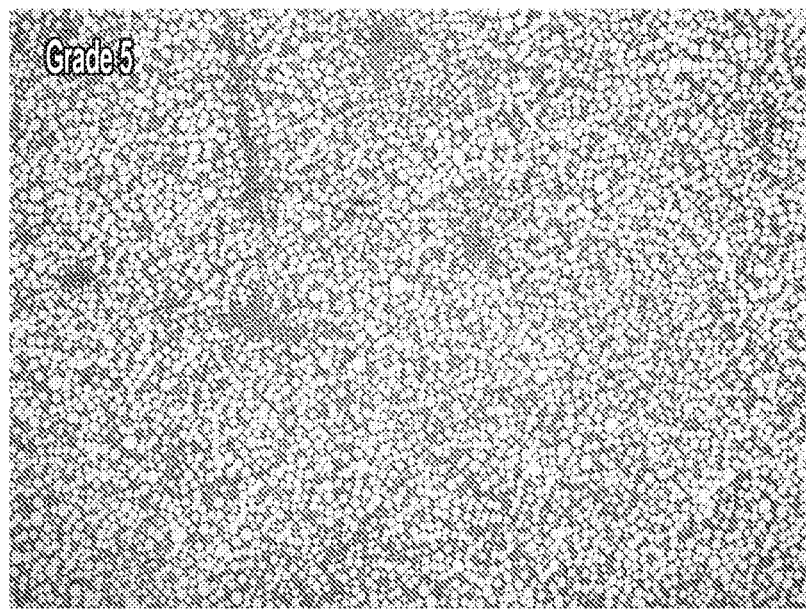
FIG. 5E: GRADE 5=Severe/many/large vacuoles, diffuse, all liver regions affected.

The study groups as described in Example 1 were further evaluated with regard to the development of liver weight versus body weight. An increase in liver weight which is not proportional to the increase of body weight is typical for the development of liver damage, specifically steatosis, as described before. FIG. 4 shows the results for the liver to body weight ratio in percent again for those groups of animals that received only saline solution, LE 10%, and the same lipid emulsion with choline derivatives added in concentration as described before ("high": 31 mmol/L). As can be seen, the administration of a lipid emulsion alone leads to an increase in said ratio, indicating a gain in liver weight due to liver damage (steatosis). The addition of choline chloride or CDP-choline both lead to a reduction of the ratio and thus an improvement of the liver status. However, the most pronounced reduction of the ratio is again achieved with GPC. Again, phosphatidylcholine which is contained in the lipid emulsion(s) does not seem to have any effect.

Example 5: Stability of lipid emulsions in the presence of choline derivatives Besides investigating into the efficacy of choline derivatives in addressing liver damage, the lipid emulsions prepared as described in Example 1 were further assessed for their respective stability after sterilization (see Table V). It was found that the stability of the lipid emulsions was improved in the presence of GPC compared to choline chloride or CDP-choline. In fact, choline chloride and CDP-choline were found to destabilize the lipid emulsions during sterilization (heat). Lipid emulsions containing either choline chloride or CDP-choline resulted in a phase separation of the lipid emulsions during sterilization. In the presence of GPC, the lipid emulsions remained stable.

TABLE V

Stability of lipid emulsions upon sterilization
in the presence of different choline derivatives

| Choline Derivative | Concentration (mmol/L) | Lipid Emulsions tested: LE (%) | Comment |
|---|---|---|---|
| Choline Chloride | 15 | 10, 13, 20 | Phase separation during sterilization |
| Glycero-phosphocholine | 30 | 10, 20 | Stable emulsion |
| CDP-choline | 30 | 10 | Phase separation during sterilization |

The invention is claimed as follows:

1. A lipid emulsion for parenteral administration, comprising (1) glycerophosphocholine (GPC) in a concentration of from 0.1 g to 15.0 g per liter, (2) docosahexaenoic acid (DHA) and (3) arachidonic acid (ARA),
   wherein the lipid emulsion comprises an aqueous phase and between 5% to about 35% by weight of an oil phase based on the total weight of the lipid emulsion,
   wherein the lipid emulsion comprises the DHA in a concentration of from 0.1 g to 5.0 g per 100 g of the oil phase and the ARA in a concentration of from 0.1 g to 15.0 g per 100 g of the oil phase for use in the treatment of choline deficiency and liver damage by parenteral administration, and
   wherein the lipid emulsion is essentially free of eicosapentaenoic acid (EPA).

2. The lipid emulsion for parenteral administration according to claim 1, wherein GPC is comprised in a concentration of from 2.0 g to 12.0 g per liter.

3. The lipid emulsion for parenteral administration according to claim 1, wherein GPC is comprised in a concentration of from 0.5 g to 5.0 g per liter.

4. The lipid emulsion according to claim 1, wherein the lipid emulsion comprises docosahexaenoic acid (DHA) in a concentration of from 0.25 g to 3.0 g per 100 g of oil phase.

5. The lipid emulsion according to claim 1, wherein the lipid emulsion comprises arachidonic acid (ARA) in a concentration of from 1.5 g to 7.5 g per 100 g of oil phase.

6. A method of treating a patient who requires parenteral nutrition when oral and enteral nutrition is not possible, insufficient or contraindicated, the method comprising administering to the patient the lipid emulsion according to claims 1.

7. The method according to claim 6, wherein the patients suffer from choline deficiency.

8. The method according to claim 6, wherein the patients are pediatric or adult patients.

9. The method according to claim 6, wherein the patients suffer from liver steatosis.

10. The lipid emulsion for parenteral administration according to claim 1, wherein the lipid emulsion comprises no more than 0.001% of the EPA.

11. A multi-chamber container for providing a parenteral nutrition formulation, wherein the multi-chamber container comprises a first chamber containing a lipid emulsion according to claim 1.

12. The multi-chamber container according to claim 11, wherein the multi-chamber container has a second chamber containing an amino acid formulation or a carbohydrate formulation.

13. The multi-chamber container according to claim 12, wherein the second chamber contains an amino acid formulation and wherein a third chamber contains a carbohydrate formulation.

14. The multi-chamber container for parenteral administration according to claim 13, wherein the multi-chamber container has a fourth chamber containing vitamins or trace elements.

15. The multi-chamber container for parenteral administration according to claim 14, wherein the fourth chamber contains vitamins and a fifth chamber containing trace elements.

16. A parenteral nutrition composition comprising a lipid emulsion, the lipid emulsion comprising:
(1) glycerophosphocholine (GPC) in a concentration of from 0.1 g to 15.0 g per liter, (2) docosahexaenoic acid (DHA) and (3) arachidonic acid (ARA),
wherein the lipid emulsion comprises an aqueous phase and between 5% to about 35% by weight of an oil phase based on the total weight of the lipid emulsion,
wherein the lipid emulsion comprises the DHA in a concentration of from 0.1 g to 5.0 g per 100 g of the oil phase and the ARA in a concentration of from 0.1 g to 15.0 g per 100 g of the oil phase for use in the treatment of choline deficiency and liver damage by parenteral administration, and
wherein the lipid emulsion is essentially free of eicosapentaenoic acid (EPA).

17. The parenteral nutrition composition according to claim 16, wherein GPC is present in a concentration of from 0.01 g to 6.0 g per liter.

18. A parenteral nutrition composition reconstituted from a multi-chamber container comprising an amino acid formulation, a carbohydrate formulation, and a lipid formulation,
wherein glycerophosphocholine is present in the lipid formulation of the composition in a concentration of from 0.01 g to 6.0 g per liter,
wherein the lipid formulation further comprises docosahexaenoic acid (DHA) in a concentration of from 0.1 g to 5.0 g per 100 g of the oil phase and arachidonic acid (ARA) in a concentration of from 0.1 g to 15.0 g per 100 g of the oil phase for use in the treatment of choline deficiency and liver damage by parenteral administration, and
wherein the lipid formulation is essentially free of eicosapentaenoic acid (EPA).

19. A method of providing choline to a patient who requires parenteral nutrition, comprising parenterally administering a composition according to claim 1 to a patient.

20. The method according to claim 19, wherein the glycerophosphorylcholine is administered in a dose of from 15 mg/kg/day to 300 mg/kg/day.

21. The method according to claim 19, wherein the patient is a pediatric patient and glycerophosphorylcholine is administered in a dose of from 50 mg/kg/day to 150mg/kg/day.

22. The method according to claim 19, wherein the composition is provided by means of a peripherally or a centrally inserted catheter.

23. A method of preparing a lipid emulsion according to claim 1, comprising the steps of:
(a) Separately heating up the oil phase and the aqueous phase to a temperature of from about 70° C. to about 80° C. under agitation;
(b) Adding glycerophosphocholine to the aqueous phase;
(c) Preparing the pre-emulsion by transferring the oil phase to the aqueous phase under agitation;
(d) Homogenizing the pre-emulsion at a temperature of from about 40° C. to 60° C. under pressure;
(e) Optionally adding water to adjust the required volume and concentrations;
(f) Optionally adjusting the pH to a range of from about 7.8 to 8.8; and
(g) Optionally sterilizing the lipid emulsion.

24. The method according to claim 23, wherein at least steps (a) to (d) are performed in the presence of an inert gas, preferably $N_2$.

25. The method according to claim 23, wherein the lipid emulsion is sterilized by heat.

* * * * *